United States Patent [19]

Rinehart

[11] Patent Number: 5,294,603
[45] Date of Patent: * Mar. 15, 1994

[54] PHARMACEUTICAL COMPOSITIONS CONTAINING DIDEMNINS

[75] Inventor: Kenneth L. Rinehart, Urbana, Ill.

[73] Assignee: The Board of Trustees of The University of Illinois, Urbana, Ill.

[*] Notice: The portion of the term of this patent subsequent to Nov. 1, 2005 has been disclaimed.

[21] Appl. No.: 837,803

[22] Filed: Feb. 18, 1992

Related U.S. Application Data

[60] Continuation-in-part of Ser. No. 482,372, Feb. 20, 1990, Pat. No. 5,137,870, which is a division of Ser. No. 137,484, Dec. 23, 1987, Pat. No. 4,950,649, which is a continuation-in-part of Ser. No. 894,442, Jul. 31, 1986, abandoned, which is a continuation of Ser. No. 663,824, Oct. 22, 1984, abandoned, which is a continuation of Ser. No. 449,296, Dec. 13, 1982, abandoned, which is a continuation of Ser. No. 299,894, Sep. 8, 1981, abandoned, which is a division of Ser. No. 217,768, Dec. 18, 1980, abandoned, which is a continuation-in-part of Ser. No. 186,932, Sep. 12, 1980, abandoned.

[51] Int. Cl.$^5$ .................. C07K 5/12; A61K 37/00
[52] U.S. Cl. ............................ 514/10; 514/11
[58] Field of Search .............. 514/10, 11; 530/317

[56] References Cited

U.S. PATENT DOCUMENTS

| | | | |
|---|---|---|---|
| 4,782,135 | 11/1988 | Rinehart, Jr. | 530/317 |
| 4,950,649 | 8/1990 | Rinehart | 514/10 |
| 5,137,870 | 8/1992 | Rinehart | 514/10 |

*Primary Examiner*—Nathan M. Nutter
*Attorney, Agent, or Firm*—Ernest V. Linek

[57] ABSTRACT

This invention is directed to didemnin derivatives, including N-acyl congeners of didemnin A (DA); several DDB-type analogues of DA in which either pyruvic acid has been replaced (with phenylpyruvic acid or alphaketobutyric acid) or proline at position 8 has been replaced [with L-azetidine-2-carboxylic acid (AZT), L-pipecolic acid (Pip), 1-amino-1-carboxylic cyclopentane (acc$^5$), D-Pro or sarcosine (sar); and other cyclic depsipeptides related to the didemnins, which were isolated from a relatively polar extract of the tunicate T. solidum; namely the didemnins—X [(R)-3-hydroxy-decanoyl-(Gln)$_3$-Lac-Pro didemnin A]; Y [(R)-3-hydroxy-decanoyl-(Gln)$_4$-Lac-Pro didemnin A]; M (pGlu-Gln-Lac-Pro-didemnin A); N ([Tyr$^5$] didemnin B); nordidemnin N ([Tyr$^5$] nordidemnin B); and epididemnin A ([2S,4R-Hip$^2$] didemnin A).

7 Claims, No Drawings

PHARMACEUTICAL COMPOSITIONS CONTAINING DIDEMNINS

STATEMENT OF GOVERNMENT SUPPORT

This invention was made with government support under Grant No. AI-4769 awarded by the National Institutes of Health. Thus, the government of the United States has certain rights in this invention.

CROSS-REFERENCE TO RELATED APPLICATIONS

This application is a continuation-in-part of copending application Ser. No. 07/482,372, filed Feb. 20, 1990, now U.S. Pat. No. 5,137,870, which in turn is a divisional of Ser. No. 07/137,484, filed Dec. 23, 1987, which in turn is a continuation-in-part of Ser. No. 06/894,442, filed Jul. 31, 1986, now abandoned, which in turn is a continuation of Ser. No. 06/663,824, filed Oct. 22, 1984, now abandoned, which in turn is a continuation of Ser. No. 06/449,296, filed Dec. 13, 1982, now abandoned, which in turn is a continuation of Ser. No. 06/299,894, filed Sep. 8, 1981, now abandoned, which is a divisional of Ser. No. 06/217,768, filed Dec. 18, 1980, now abandoned, which is a continuation-in-part of Ser. No. 06/186,932, filed Sep. 12, 1980, now abandoned.

The disclosures of the above-referenced patents and applications are hereby incorporated herein by reference.

BACKGROUND OF THE INVENTION

The didemnins (A, B, C, D, E, X and Y) are members of a novel class of cyclic depsipeptides isolated from the Caribbean tunicate *Trididemnum solidum* (family Didemnidae). See, Rinehart, K.L., et al., *J. Nat. Prod.*, 1988, 51, 1.

These peptides exhibit a wide variety of biological activities both in vivo and in vitro including antiviral, antitumor, antiproliferative and immunosuppressive activities.

SUMMARY OF THE INVENTION

The present invention provides several derivatives of the various didemnins, which have been synthesized to provide less toxic and more efficacious therapeutic agents.

Based on the hydrophobic structure of didemnin B and its pleiotropic effects on cellular metabolism, the plasma membrane has been proposed as a potential site of action for the didemnins. See, Legrue, S. J., et al., *Lymphokine Research*, 1988, 7, 21. Thus it was believed that increasing the lipophilicity of didemnin A, might raise its solubility in the plasma membrane and thereby increase its activity. Since N-acetyl didemnin A, was known to be as active as didemnin B, it was felt that the N-amine of N-methyl D-leucine positions would be an excellent position for the addition of hydrophobic groups to didemnin A.

This led to the synthesis of a series of N-acylated analogues of didemnin A consisting of alkyl chains with 2, 3, 4, 5, 7, 11, 15 and 17 carbon atoms with view to determining the optimal hydrophobicity required for the biological activity. Thus, in one embodiment of the present invention, the synthesis, cytotoxicity and antiviral activity of a number of N-acyl congeners of didemnin A are provided.

Another embodiment of the present invention involves a cyclic depsipeptide structurally related to didemnin, namely, dehydrodidemnin B (DDB), which is obtained from the Mediterranean tunicate *Aplidium albicans*. Structurally, DDB is a simple N-substituted derivative of didemnin A (DA), having Pyruv-Pro attached to D-N-methylleucine position of DA.

The structure of DDB is also very similar to that of didemnin B (DB) except for pyruvic acid at position 9 instead of lactic acid. In addition, DDB was found to be several times more active than DB in antiviral (HSV-1 in CV-1 cells) and cytotoxicity (L1210 leukemia cells) assays in vitro. Further DDB has shown great potential as an antitumor agent against P388 leukemia, B16 melanoma and Lewis lung cancer in vivo.

The significant differences exhibited in the biological activities of DB and DDB is in agreement with a previous discovery that simple N-substituted derivatives of Didemnin A with different linear acyl groups can exhibit tremendous variation in their biological activity. The high order of biological activity exhibited by DDB led to the structure-activity relationship studies provided herein, especially with reference to the Pyruv$^9$-Pro$^8$ unit with the goal being the development of more effective chemotherapeutic agents.

Thus, in another embodiment of the present invention, several DDB-type analogues of DA were synthesized in which either pyruvic acid has been replaced (with phenylpyruvic acid or -ketobutyric acid) or proline at position 8 has been replaced [with L-azetidine-2-carboxylic acid (AZT), L-pipecolic acid (Pip), 1-amino-1-carboxylic cyclopentane(acc$^5$), D-Pro or sarcosine (sar)].

In the final embodiment of the present invention, several cyclic depsipeptides related to the didemnins were isolated from a relatively polar extract of the tunicate *T. solidum*. The structure of these didemnins were determined by spectroscopic techniques and chemical degradations as follows; didemnins—X [(R)-3-hydroxy-decanoyl-(Gln)$_3$-Lac-Pro didemnin A]; Y [(R)-3-hydroxy-decanoyl-(Gln)$_4$-Lac-Pro didemnin A]; M (pGlu-Gln-Lac-Pro-didemnin A); N ([Tyr$^5$] didemnin B); nordidemnin N ([Tyr$^5$] nordidemnin B); and epididemnin A ([2S, 4R-Hip$^2$] didemnin A).

In addition, several new didemnin analogues were prepared semisynthetically. Structure elucidation, chemical conversion, biological activities including cytotoxicity, antiviral and immunosuppressive activities and structure-activity relationships for these compounds are described herein.

DETAILED DESCRIPTION OF THE INVENTION

The organism from which didemnins and nordidemnins are extracted is a colonial marine tunicate of the family Didemnidae Trididemnum sp. These organisms are in the suborder Aplousobranchia of the order Enterogana of the class Ascidiacea of the subphylum Urochordata of the phylum Chordata. They can be readily obtained by scuba techniques at depths of 10 to 100 feet where they encrust rocks, sponges, gorgonians, etc., in colony sizes up to 3 feet in diameter and ¼ inch in thickness. They vary in color depending on location from green-white to purple-white to brown-white to orange-white.

As described above, structure activity relationship studies were conducted on the didemnins in order to develop more potent therapeutic agents. In this first embodiment of the present invention, three sets of congeners of didemnin A were synthesized.

1st Set of Congeners

Seven hydrophobic analogues of didemnin A were synthesized by incorporating acyl chains therein, ranging from 4 to 18 carbons. The compounds synthesized were:
N-butyryl didemnin A
N-pentanoyl didemnin A
N-hexanoyl didemnin A
N-octanoyl didemnin A
N-lauroyl didemnin A
N-palmitoyl didemnin A
N-stearoyl didemnin A

2nd Set of Congeners

Three analogues of didemnin A were also synthesized in which the amino acids at positions 1, 5, and 6 were replaced with their corresponding D-amino acids. The compounds formed were:
D-Thr$^1$] didemnin A
D-Pro$^5$] didemnin A
D-MeTyr(Me)$^6$] didemnin A

3rd Set of Congeners

Five didemnin A analogues related to dehydrodidemnin B (DDB, see below) were synthesized by introducing DDB-type modifications into their linear peptide chain moieties. The DDB-type compounds formed were:
Phenylpyruv-Pro didemnin A
Pyruv-Sar didemnin A -ketobutyryl-Pro didemnin A
Pyruv-Azt didemnin A
Pyruv-D-Po didemnin A

N-ACYL ANALOGS OF DIDEMNIN A

The cytotoxic activity and antiviral activity of N-acyl didemnin A analogues is shown in Table I and is compared with didemnin A, didemnin B, and N-acetyl didemnin A.

TABLE 1

Cytotoxicity and antiviral activity of didemnins

| Compounds$^a$ | Cytotoxicity percent L1210 inhibition dose (ng/mL) | | | | Antiviral Activity against HSV-1 dose (ng/well) | |
|---|---|---|---|---|---|---|
| | 25 | 12.5 | 5 | 2.5 | 100 | 10 |
| N$^a$-Propionyl-DA | 95 | 95 | 93 | 89 | ++ | +/− |
| N$^a$-Pentanoyl- | 91 | 81 | 56 | 25 | + | − |
| N$^a$-Hexanoyl- | 92 | 89 | 73 | 69 | + | − |
| N$^a$-Octanoyl- | 94 | 93 | 89 | 13 | − | − |
| Didemnin A | 25 | 19 | 0 | 0 | − | − |
| Didemnin B | 95 | 95 | 93 | 89 | +++ | +/− |
| N$^a$-Acetyl-DA | 94 | 93 | 89 | 38 | +++ | +/− |

$^a$Data for inactive stearoyl, palmitoyl, and lauroyl derivatives are not included.

Although the propionyl, pentanoyl, hexanoyl and octanoyl derivatives retained the cytotoxicity of didemnin B, the lauroyl, palmitoyl, and stearoyl derivatives were inactive. At lower concentrations such as 2.5 ng/ml, however, only propionyl didemnin A exhibited activity equivalent to that of didemnin B, whereas pentanoyl, hexanoyl and octanoyl derivatives were slightly less active than didemnin B.

The biological activity profile of propionyl didemnin A looked more or less like that of didemnin B even at lower concentrations. These results clearly suggest that the hydrophobicity of propionyl, pentanoyl, hexanoyl, and octanoyl derivatives appears to be sufficient for them to be partitioned into the membrane. The loss of activity in lauroyl, palmitoyl, and stearoyl derivatives may be attributed either to their fast degradation by cells or to changes in the conformation of didemnin A induced by the long hydrophobic chains. In any event derivatization of the D-N-methylleucine of didemnin A significantly affects the cytotoxicity of didemnins and considerable modification can be made at that position to provide agents of therapeutic importance.

Synthesis of N-acyl analogues was carried out in solution. Acyl groups were introduced at the N-methyl-D-leucine unit of didemnin A using a symmetrical anhydride procedure with $C_6$ to $C_{18}$ fatty acids, a 15-fold excess of symmetrical anhydride was required in order to achieve complete acylation. Propionic butyric and pentanoic acids could be introduced using a 3–5 fold excess of their symmetrical anhydride.

The symmetrical anhydrides of fatty acids were prepared in the conventional manner using EDC. Acylation of didemnin A was carried out in the presence of a catalytic amount of dimethylamino pyridine (DMAP). All analogues were purified on a silica gel column using methanol/chloroform as a eluant. They were characterized using $^1$H NMR spectroscopy and HRFABMS.

As evident from the bioactivity results at 25 ng/ml (Table 1), the $C_3$, $C_5$, $C_6$ and $C_8$ derivatives retained the full cytotoxicity of Didemnin B. However, the $C_{12}$, $C_{16}$, and $C_{18}$ derivatives turned out to be mostly inactive. At a lower concentration such as 5 ng/ml, the $C_3$ and $C_8$ derivatives exhibited activity equivalent to that of Didemnin B, whereas the $C_5$ and $C_6$ derivatives were slightly less active than Didemnin B. The biological activity profile of the $C_3$ derivative looked more or less like that of Didemnin B, even at lower concentrations.

These results clearly suggest that the hydrophobicity of the $C_3$, $C_5$, $C_6$ and $C_8$ derivatives appears to be sufficient for them to be partitioned into the plasma membrane. The loss of activity in $C_{12}$, $C_{16}$ and $C_{18}$ derivatives may be attributed either to their fast degradation by cells or to changes in the conformation of Didemnin A induced by the long hydrophobic chains. Thus, derivatization of N-methyl-D-leucine of Didemnin A significantly affects the cytotoxicity of didemnins and considerable modification can be made at that position to afford agents of therapeutic importance.

GENERAL PROCEDURE FOR THE SYNTHESIS OF N-ACYL DIDEMNIN A

1-Ethyl-3-(3-dimethylaminopropyl)carbodiimide (or "EDC," 61 mg, 0.31 mmole) was added with stirring to a cooled solution of a linear aliphatic acid containing 6, 8, 12, 16 or 18 carbon atoms (0.63 mmole) in dry $CH_2Cl_2$ (1 ml). The clear solution of the symmetrical anhydride was allowed to stir at 10°–15° C. for 2 hr., then didemnin A (30 mg, 0.031 mmol) was added. The reaction mixture was left in the refrigerator for 20 hr. After that, another 5-fold quantity of the symmetrical anhydride of the fatty acid prepared by treating the acid (0.31 mmol) with EDC (30.5 mg, 0.16 mmol) was added, followed by dimethylaminopyridine (DMAP, 5 mg). The reaction mixture was again left in the refrigerator for 24 hr., then diluted with $CH_2Cl_2$ and washed with 5% $NaHCO_3$ and with water to neutral pH. The organic layer was dried and evaporated to dryness. The crude product so obtained was purified on a silica gel column using $MeOH/CHCl_3$ as an eluant to give the chromatographically homogenous product in 85–90% yield.

A: N-Acyl didemnin A (Hexanoyl, Octanoyl, Dodecanoyl, Hexadecanoyl, Octadecanoyl Derivatives)

A solution of the free acid (0.63 mmol) dissolved in $CH_2Cl_2$ (2 ml) was cooled to 10° C. and EDC (0.31 mmole) was added with stirring. The clear solution was stirred at 10° C. for 1.5 hr., then didemnin A (0.31 mmole) was added and the solution was stirred at 10° C. for 2 hr., then left in freezer overnight. After 16 hr. 5 mg of DMAP was added and the reaction mixture was left in the freezer for 20 hr. Next (0.31 mmole) of another batch of free acid preactivated with EDC (0.15 mmole) was added and the reaction mixture was again left at 0° C. for 24 hr. Solvent was evaporated, the residues taken up in EtOAc, washed with 5% aq. $NaHCO_3$ and water and the organic layer was dried over $Na_2SO_2$ and evaporated to dryness. The crude material was purified on a silica gel column using 3–5% MeOH in $CHCl_3$ as eluant.

B: N-Pentanoyl didemnin A

Pentanoic acid (0.019 g, 0.19 mmole) was dissolved in dry $CH_2Cl_2$ (2 ml) and treated with EDC (0.018, 0.09 mmole) at 10° C. for 1.5 hr. To this didemnin (30 mg, 0.32 mmole) was added and the clear solution was left at 0° C. overnight. DMAP (2 mg) was added and the reaction mixture was left at 0° C. for 48 hr. Solvent was evaporated and the product was taken up in EtOAc, washed with 5% aq. citric acid, water, 5% aq. $NaHCO_3$ and finally with water the solution was dried over $NaSO_4$ and evaporated to dryness. The product N-pentanoyldidemnin A, was purified on a silica gel column using 2% MeOH in $CHCl_3$ as eluant to yield mg (9%).

C: N-Butyric didemnin A

N-Butyric anhydride (0.01 g, 0.63 mmole) was added to a solution of didemnin A (30 mg) in $CH_2Cl_2$ (2 ml) at 0° C. followed by DMAP (2 mg). The clear solution was left at 0° for 48 hr. taken up in EtOAc and washed with 5% $NaHCO_3$ and water, then dried over $Na_2SO_4$ and evaporated to dryness. The residue was chromatographed on a silica gel column using 2% MeOH to yield 0.29 mg, (85%).

D: Propionyl didemnin A

Propionic acid (31 mg) and dicyclohexyl carbodiimide (45 mg) were dissolved i methylene chloride (5 ml) and left at 0° C. for 90 min. The dicyclohexylurea was filtered off and the filtrate added to didemnin A (199 mg). After a further 16 hours at 0° the product was blown dry under nitrogen and then purified by reversed phase HPLC (using 77.23 methanol-water solvent at 2.5 ml/minute and 245 nm UV detection) to give N-propionyl-didemnin A (134 mg, 64°1.) $[\alpha]_D^{25} = -74.8°$ (c, 4.0; $CHCl_3$); Anal. Calcd. for $C_{52}H_{83}N_6O_{13}$ (M+H); mol. wt. 999.6018; Found: Mol. wt. 999.5985 (M+H, HRFABMS).

E: L-Prolyl didemnin A

Benzyloxycarbonyl-L-proline (23 mg) and dicyclohexylcarbodiimide (10 mg) were dissolved in methylene chloride (2 ml) and left at 0° for 90 min. The dicyclohexylurea was then filtered off and the filtrate added to didemnin A (43 mg). After a further 16 hours at 0° the product was blown dry under nitrogen. A FAB mass spectrum of this product showed the desired peak for benzyloxycarbony-L-prolyl-didemnin A (117, M+H). The material (70 mg) was then hydrogenated in methanol (10 ml) with 5% palladium on charcoal (25 mg) for 16 hours. After filtration the crude product (54 mg) was purified by reversed phase HPLC (77:23: methanol:water solvent buffered at pH 7.5 with ethyl acetate/triethylamine, 2.5 ml/minute flow, 254 nm UV detection) to give N-prolyl didemnin A (7 mg; 15%), $[\alpha]_D^{25} = -47.7°$ (c, 0.35; $CHCl_3$).

SYNTHESIS OF [D-Thr¹] DIDEMNIN A

Z-D-MeLeu-D-Thr-OTMSe

To a solution of Z-D-MeLeu (0.27 g, 1 mmol) and H-D-Thr-OTMSe (0.219 g, 1 mmol) in dry $CH_2Cl_2$ (8 ml), N-hydroxysuccinimide (0.11 g, 1 mmol) and EDC (0.191 g, 1 mmol) were added at 0° C., the clear solution was stirred at 0° C. for 6 hrs. then was left in the freezer overnight. Solvent was evaporated to dryness and the residue was taken up in EtOAc. The organic layer was washed with 5% aq. citric acid, water 5% aq. $NaHCO_3$ and water to neutral pH, then dried over $Na_2SO_4$ and evaporated to dryness. The crude product so obtained was purified on a silica gel column using $CHCl_3$—5% MeOH in $CHCl_3$ as the eluant; yield, 0.21 g (43%); $R_f$ 0.3 ($CHCl_3$ MeOH 19:1), $[\alpha]_D^{25} = 19.2°$ (c, 0.5, MeOH); Anal. Calcd. for $C_{24}H_{41}N_2O_6S$: $M_r$ 481.2729; (M+H); Found: $M_r$ 421.2734 (HRFABMS).

BOC-MeTyr(Me)-OH

To a solution of BOCTyr-OH (0.562 g, 2 mmol) in dry THF at 0° C. $CH_3I$ (2.8 g, 20 mmol) and NaH (0.24 g, 10 mmol) were added with vigorous stirring. The reaction mixture was stirred at r.t. for 24 hrs., then chilled, and NaH was destroyed by added EtOAc with water. The clear solution was evaporated to dryness and the residue was taken up in 10 ml of water. The aqueous solution was extracted with ether (2×10 ml), acidified with citric acid and extracted with EtOAc. The organic layer was washed with 5% hypo solution and water, dried over $Na_2SO_4$ and evaporated to dryness. The product was obtained as an oil: yield 0.56 g (91%); FABMS m/z 310 (M+H): 10. 0.5:0.5 $R_f$ 51 ($CHCl_3$: MeOH: AcOH); Anal. Calcd. for $C_{16}H_{24}NO_4$: $M_r$ 310.1663 (M+H); Found: $M_r$ 310.1654 (M+H) (HRFABMS).

Z-MeD-Leu-D-Thr-OTMSe BOC-MeTyr(Me)

To a solution of BOC-MeTyr(Me) (0.103 g, 0.33 mmol) and Z-MeD-Leu-Thr-OTMSe (0.160 g, 0.33 mmol) in dry $CH_2Cl_2$, 5 ml), DCC (0.07 g, 0.35 mmol) and catalytic amount of DMAP (4 mg) was added at 0° C. The reaction mixture was stirred at 0° C. for 2 hrs. and then left for overnight stirring at r.t. DCU was filtered off and the filtrate was evaporated to dryness. The residue was taken up in EtOAc and washed with 5% aq. $NaHCO_3$ and water. It was dried over $Na_2SO_4$ and then evaporated to dryness. The crude product was then purified to an oil on silica gel column using EtOAc-hexane (30%) as an eluant. Yield 0.23 g (80%), FABMS m/z 772.3 (M+H), $R_f$ 0.42 (20% EtOAc-hexane); $[\alpha]_D^{25} = +40.1°$ (c, 0.4; MeOH); Anal. Calcd. for $C_{40}H_{62}N_3O_{10}Si$: $M_r$ 772.4201 (M+H); Found: 772.4204 (M+H) (HRFABMS).

BOC-Pro-OTMSe

To a solution of BOC-Pro (0.5 g, 2.3 mmol) and TMSe-OH (0.3 ml) in dry $CH_2Cl_2$ (10 ml), DCC (0.55 g, 2.4 mmol) and DMAP (29 mg) was added at 0° C. The reaction mixture was stirred at 0° C. for 2 hrs. then left in refrigerator overnight. DCU was filtered off and filtrate was evaporated to dryness. The residue was taken up in EtOAc and washed with 5% NaHCO$_3$ and finally with water till neutral pH. The organic layer was dried over Na$_2$SO$_4$ and evaporated to dryness. The product was obtained as an oil. Yield: 0.7 g, 95% FABMS (M+H) 316.1.; R$_f$=0.61 (CHCl$_3$); [α]$_D^{25}$ = −50.1 (c, 1; CHCl$_3$); Anal. Calcd. for C$_{15}$H$_{30}$NO$_4$Si M2 316.1885 (M+H); Found: M$_r$ 316.1865 (M+H) (HRFABMS).

Bn-Hip-Leu-OTMSe

Crude Bn-Hip-Leu-OTMSe was purified on a silica gel column using CHCl$_3$—5% MeOH-CHCl$_3$ as an eluant. The product was obtained as oil. FABMS (M+H) 478.2; Anal. Calcd. for C$_{26}$H$_{45}$NO$_5$Si, M$_r$ 478.2990 (M+H); Found: 478.2988 (M+H) (HRFABMS); [α]$_D^{25}$= −47.5 (c, 0.1, CHCl$_3$); R$_f$=0.56 (5% MeOH—CHCl$_3$).

Bn-Hip-Leu-OH

Bn-Hip-Leu-OTMSe (0.28 g, 0.6 mmol) in dry THF (2 ml) was treated with a 1M solution of Bu$_4$NF in THF (2 ml). The clear solution was left at r.t. for 1½ hrs. After that the reaction was quenched by adding a few drops of water. Solvent was evaporated and residue was dissolved in aq. NaHCO$_3$ (5 ml). The aq. layer was extracted with Et$_2$O and then acidified with citric acid. The product was extracted in EtOAc and washed with water till neutral pH. It was dried over Na$_2$SO$_4$ and evaporated dryness to yield Bn-Hip-Leu as an oil. Yield 0.222 g, (95%); FABMS m/z 378.3 (M+H); Anal. Calcd. for C$_{21}$H$_{32}$NO$_5$: M$_r$ 378.2284 (M+H); Found: M$_r$ 378.2280 (M+H) (HRFABMS); [α]$_D^{25}$= −41.0 (c, 0.2, CHCl$_3$).

Bn-Hip-Leu-Pro-OTMSe

BOC-Pro-OTMSe (0.183 g, 0.58 mmol) was treated with 4N HCl/dioxane (2 ml) for 30 min. at r.t. After that it was evaporated to dryness in vacuo to afford HCl.Pro-OTMSe This was taken up in DMF (2 ml) and neutralized with NMM (0.065 ml) at 0° C.

In another flask Bn-Hip-Leu (0.212 g, 0.28 mmol) and HOBt (0.089 g, 0.58 mmol) were dissolved in dry CH$_2$Cl$_2$ (2 ml) and dry DMF (1 ml) and to this DCC (0.120 g, 0.58 mmol) was added at 0° C. After 10 min. Pro-OTMSe was added to it. The solution was stirred at 0° C. for 1 hr. and then left for overnight stirring at r.t. DCU was filtered off and the filtrate was evaporated to dryness. The residue was taken up in EtOAc and washed with 5% aq. citric acid, water, 5% NaHCO$_3$ and finally with water till neutral pH. It was then dried over Na$_2$SO$^4$, and evaporated to dryness. It was purified on silica gel calcium using gradient of CHCl$_3$—2.5% MeOH-CHCl$_3$ Yield 0.3 g, (89%); R$_f$ 0.51 (2.5% MeOH-CHCl$_3$); FABMS m/z 575.3 (M+H); Anal. Calcd. for C$_{31}$H$_{51}$N$_2$O$_6$Si: M$_r$ 575.3516. (M+H); Found: M$_r$ 575.3524 (M+H) (HRFABMS) [α]$^{25}$$_D$= −56.49 (c, 0.2, CHCl$_2$).

Hip-Leu-Pro-OTMSe

Bn-Hip-Leu-Pro-OTMSe (0.5 g) was dissolved in MeOH (20 ml) and AcOH (1 ml) followed by addition of 10% Pd/C (70 mg). H$_2$ was bubbled under vigorous stirring for 12 hrs. The catalyst was filtered off and solvent was evaporated to dryness. Yield 0.4 g, (95%) FABMS m/z 485.3 (M+H); Anal. Calcd. for C$_{24}$H$_{45}$N$_2$O$_6$Si, M$_r$ 485.3049 (M+H); Found, M$_r$ 485.3047 (M+H) (HRFABMS); [α]$_D^{20}$= −59° (c, 0.1, CHCl$_3$)

BOC-Isl-OH

BOC-Isl-OEt (1 g, 3.3 mmol) was dissolved in EtOH (10 ml) followed by addition of 2N NaOH (1.6 ml). The clear solution was stirred for 1 hour at r.t. and then evaporated in vacuo. The residue was dissolved in water and extracted with Et$_2$O. The aq. layer was then acidified with citric acid. It was extracted with EtOAc and washed with water until neutral pH. EtOAc layer was dried over Na$_2$SO$_4$ and evaporated to dryness to afford BOC-Isl as an oil 0.88 g, (95%).

BOC-Isl-(TBDMS)-OTBDMS

BOC-Isl (0.88 g, 3.2 mmol) was treated with TBDMS-Cl (1.44 g, 9.6 mmol) and imidazole (1.3 g, 19.2 mmol) in dry DMF (10 ml). The reaction mixture was stirred at r.t. for 16 hrs. After that, the DMF was evaporated and residue was taken up in EtOAc and washed with 5% NaHCO$_3$ and water. It was dried over Na$_2$SO$_4$ and evaporated to dryness. Yield 1.6 g, 95% FABMS.

BOC-Isl-(TBDMS)-OH

BOC-Isl-(T)-OT (1.5 g) was dissolved in THF-AcOH-H$_2$O (3:3:1) 10 ml and left for overnight stirring. After that solvent was evaporated and residue was taken up in EtOAc and washed with water till neutral pH. It was dried over Na$_2$SO$_4$ and evaporated to dryness. Yield 1.0 g, (90%); FABMS 390 (M+H) R$_f$ 0.41 (CHCl$_3$:MeOH:AcOH) 19:1:0.5).

BOC-Isl-(TBDMS)-Hip-Leu-Pro-OTMSE

BOC-Isl(T) (0.38 g, 0.97 mmol) and Hip-Leu-Pro-OTMSe (0.43 g, 0.88 mmol) were dissolved in dry CH$_2$Cl$_2$ (6 ml) and dry DMF (2 ml). The solution was chilled to 0° C. and DEC (0.201 g) was added in presence of DMAP (12 mg). The solution was stirred at 0° to 2 hrs. and then left at r.t. for overnight stirring. After that DCU was filtered off and filtrate was evaporated to dryness. The residue was taken up in EtOAc washed with 5% NaHCO$_3$ and water. It was dried over Na$_2$SO$_4$ and evaporated to dryness. The crude product was chromatographed on a silica gel column using a gradient of CHCl$_3$—4% MeOH:CHCl$_3$ as an eluant. Yield 78%; FABMS m/z 856.4 (M+H); R$_f$ 0.54 (5% MeOH-CHCl$_3$); Anal. Calcd. for C$_{43}$H$_{82}$N$_3$O$_{10}$Si$_2$: M$_r$, 856.5538 (M+H); Found; M$_r$, 856.6620 (HRFABMS); [α]$_D^{26}$= −72.61 (C, 0.1; CHCl$_3$).

Z-D-MeLeu-D-Thr-OTMSe

BOC-Isl-(TBDMS)-Hip-Leu-Pro-MeTyro (ME)

BOC-Isl-(T)-Hip-Leu-Pro-OTMSE (40 mg, 0.04 mmol) was dissolved in 0.5 ml of dry DMF followed by addition of 2M Bu$_4$NF/DMSO (0.7 ml). The clear solution was left at r.t. for 20 hrs. After that it was taken up in EtOAc and washed with 5% citric acid several times and finally with water. The organic layer was dried over Na$_2$SO$_4$ and evaporated to dryness yield 28 mg (75%).

Z-D-MeLeu-D-Thr-OTMSe BOCMeTyr(Me)

Thr-OTMSe BOCMeTyr(Me) (0.026 g, 0.03 mmol) was dissolved in dioxane (1 ml) and treated with 6%

HCl/dioxane (1 ml) for 30 minutes at r.t. After that it was evaporated to dryness. The resulting hydrochloride sat was treated with Et₃N (5 μl) in DMF (1 ml). To this solution BOC-Isl(T)-Hip-Leu-Pro-OH obtained above was added in CH₂Cl₂ (0.3 ml). This was followed by addition of BOP-Cl (9.2 mg, 0.037 mmol) and Et₃N (10 μl) at 0° C. The reaction mixture was stirred at 0° C. for 72 hrs. and then evaporated. The crude product was dissolved in EtOAc and washed with 5% citric acid, water and 5% NaHCO₃ and finally with water It was dried over Na₂SO₄ and then evaporated to dryness. It was purified on preparative silica gel plates using 10% MeOH-CHCl₃ as eluant. Yield, 29 mg (61%) FABMS m/z 1409.5 (M+H); $[\alpha]_D^{25} = -41°$ (c, 0.2; MeOH).

Z-[D-Thr¹] didemnin A

The protected heptapeptide was (0.022 g, 0.015 mmol) was dissolved in dry DMF (1 ml) and a 2M solution of Bu₄NF in DMSO (0.5 ml) was added to it and the clear solution was left at r.t. for 24 hrs. It was then evaporated, taken up in EtOAc and washed with 5% citric acid several times and finally with water till neutral pH. It was dried over Na₂SO₄ and evaporated to dryness. The product so obtained was dissolved in dry dioxane (1 ml) and treated with 2N HCl/dioxane (1 ml). After 1 hour the solvent was evaporated to dryness. The product was dissolved in dry DMF (0.3 ml) and treated with DPPA (3.2 ml) DMAP (0.14 mg) HOBt (1.8 mg) and Et₃N (1.6 μl). The reaction mixture was allowed to stir at 0° C. for 72 hrs. and then evaporated. It was dissolved in EtOAc and washed with water. The organic layer was dried over Na₂SO₄ and evaporated to dryness. The crude product was purified by HPLC using C₁₈ semipreparative column. Yield, 2.2 mg, (40%); FABMS m/z 1076.6 (M+H); $[\alpha]_D^{25} = -49.8$ (c, 0.2, MeOH); Anal. Calcd. for C₅₇H₈₅N₆O₁₄; M, 1077.6110 (M+H); Found, M, 1077.6124 (M+H) (HRFABMS).

[D-Thr²] didemnin A

The protected cyclic peptide Z-[D-Thr²] didemnin A (5 mg) was dissolved in MeOH (5 ml) and of Pd/C (3 mg) was added to it. H₂ was bubbled for 8 hrs. and then the catalyst was filtered off and product so obtained (more than 92% pure) was further purified on RPHPLC using C₁₈ semipreparative column using 75% MeOH-H₂O as the eluant. Yield 3.7 mg (85%); FABMS m/z 943.6 (M+H); $[\alpha]_D^{25} = -79.4$ (c. 0.2; MeOH) R, 0.63 (CHCl₃—MeOH) 19:1; Anal. Calcd. for C₄₉H₇₈N₆O₁₂: M, 943.5756 (M+H); Found, M, 943.5780 (HRFABMS).

SYNTHESIS OF [D-Pro⁵] DIDEMNIN A

Hip-Leu-OTMSe

Bn-Hip-Leu-OTMSe (0.238 g) was dissolved in MeOH and Pd/C (210%, 70 mg) was added. H₂ was bubbled to the solution 12 hrs. Then catalyst was filtered off and the filtrate was evaporated to dryness. Yield, 0.18 g (90%); FABMS m/z 388.2 (M+H); $[\alpha]_D = -37.1$ (c, 0.4, CHCl₃); R, 0.41; Anal. Calcd. for C₁₉H₃₈NO₅Se, M, 388.244 (M+H); Found: M, 388.2430 (M+H) (HRFABMS).

BOC-Isl-(TBDMS)-Hip-Leu-OTMSe

BOC-Isl-(T) (0.199 g, 0.57 mmol) and Hip-Leu-OTMSe (0.18 g, 0.46 mmol) were dissolved in dry CH₂Cl₂ (5 ml) and chilled to 0° C. To this DCC (0.015 g, 0.51 mmol) and DMAP (6.2 mg) was added under stirring. The reaction mixture was stirred at 0° C. for 4 hrs. then left over night stirring at r.t. The DCU was filtered off and solvent was evaporated to dryness. The residue was taken up in EtOAc and washed successively with 5% aq. citric acid, water, 5% aq. NaHCO₃ and water. It was dried over Na₂SO₄ and evaporated to dryness. It was purified on silica gel column using 2% MeOH-CHCl₃. Yield, 0.287 g, (82%); R,=0.35 (2% MeOH-CHCl₃); $[\alpha]_D^{25} = -43.4$ (c, 0.3; CHCl₃); FABMS m/z=760.4 (M+H); Anal. Calcd. for C₃₉H₇₉N₂O₉Si₂, M, 760.4932 (M+H). Found, M, 760.4920 (M+H) (HRFABMS).

Z-D-Me-Leu-Thr-OTMSe BOC-D-Pro-MeTyr(Me)

Z-D-MeLeu-Thr-OTMSe BOCMeTyr(Me) (0.358 g, 0.46 mmol) was dissolved in dry dioxane (3 ml) and treated with of 6% HCl/dioxane (3 ml). The clear solution was left at r.t. for 30 min. and then evaporated to dryness. The resulting hydrochloride was dissolved in dry DHF (3 ml) and neutralized with NMM (0.052 ml, 0.46 mmol) at 0° C. To this BOC-Pro (0.1 g, 0 46 mmol) in dry CH₂Cl₂ (2 ml) was added. This was followed by addition of DCC (0.075 g, 0.46 mmol) and HOBt (0.071 g, 0.46 mmol). The reaction mixture was stirred at 0° C. for 2 hrs. then left at r.t. for overnight stirring. DCU was filtered off and filtrate was evaporated to dryness. The residue was taken up in EtOAc and washed successively with 5% aq. citric acid, water, 5% aq. NaHCO₃ and finally with water. It was dried over Na₂SO₄ and evaporated to dryness. The crude product was purified on silica gel column using gradient of CHCl₃—3% MeOH-CHCl₃ as an eluant. Yield 0.19 g, (70%); R,0.56 (3% MeOH-CHCl₃); FABMS m/z 869.4 (M+H); $[\alpha]_D^{25} = -31.2°$ (c, 0.3; CHCl₃); Anal. Calcd. for C₄₅H₆₉N₄O₁₁Si: M, 869.4719 (M+H); Found, M, 869.4732 (M+H) (HRFABMS).

A-D-MeLeu-Thr-OTMSe

BOC-Isl-(T)-Hip-Leu-D-Pro-MeTyr(Me)

BOC-Isl-(TBDMS)-Hip-Leu-OTMSe (0.1 g, 0.11 mmol) was dissolved in dry THF (1 ml) and to this a 2M solution of Bu₄NF in THF (0.4 ml) was added. The clear solution was left at r.t. for 24 hrs. After that it was evaporated to dryness and residue was taken up in EtOAc. It was washed with 5% aq. citric acid and finally with water. It was then dried over Na₂SO₄ and evaporated to dryness. Yield, 0.064 g, (90%).

In another flask Z-D-MeLeu-Thr-OTMSe BOC-D-Pro-MeTyr(Me) (0.1 g, 0.11 mmol) was dissolved in dry dioxane (1 ml) and treated with 8% HCl/dioxane (1 ml) including one drop of anisole. The clear solution was left at r.t. for 30 min. It was then evaporated to dryness in vacuo. It was then dissolved in dry DHF (0.2 ml) and treated with NMM (13 ml) at 0° C. To this BOC-Isl (TBDMS)-Hip-Leu obtained above was added in dry CHCl₂ (0.3 ml) followed by addition of DCC (0.025 g, 0.12 mmol) and HOBt (0.018 g, 0.12 mmol). It was stirred at 0° C. for 2 hrs. then left in freezer overnight. It was further stirred at r.t. for 20 hrs. DCU was filtered off and solvent evaporated to dryness. The residue was taken up in EtOAc and washed successively with 5% aq. citric acid, water, 5% aq. NaHCO₃ and finally with water. The organic layer was then dried over Na₂SO₄ and evaporated. The crude product was as such subjected to cyclization.

Z-[D-Pro⁵] didemnin A

Crude acyclic peptide (90 mg) was dissolved in dry DMF (0.1 ml) and treated with a 2M solution of Bu$_4$NF in DMSO (0.1 ml). The clear solution was left at r.t. for 20 hrs. It was then evaporated and taken up in EtOAc, washed with 5% aq. citric acid and water. The organic layer was dried over Na$_2$SO$_4$ and then evaporated to dryness. The material was then treated with 5% HCl/dioxane (1 ml) for 1 hour at r.t. It was then evaporated to dryness in vacuo. The residue was then subjected to cyclization using Et$_3$N (7.4 ml), DPPA (34.5 mg,) HOBt (8.1 mg), DMAP (0.6 mg) in dry DMF (0.2 ml). The reaction mixture was allowed to stir at 0° C. for 72 hrs. It was then evaporated and residue was taken up in EtOAc and washed with 5% aq. citric acid, water 5% aq. NaHCO$_3$ and finally with water. It was dried over Na$_2$SO$_4$ and evaporated to dryness. The crude material (52 mg) was loaded on preparative silica gel plates using 7% MeOH in CHCl$_3$ and the spots appearing between R$_f$ 0.52 and 0.68 were collected and eluted with 10% MeOH-CHCl3 The crude compound (20 mg) thus obtained was then subjected to purification on semipreparative C$_{18}$ column using 85% MeOH-H$_2$O to yield 3 mg of pure Z-[D-Pro⁵] didemnin A. Yield (21%); based on the tetrapeptide; FABMS, 1077 (M+H); $[\alpha]_D^{25} = -67.2°$ (c, 0.5, MeOH).

[D-Pro⁵] didemnin A

Z-[D-Pro⁵] didemnin A (2.9 mg) was dissolved in MeOH (4.5 ml) followed by the addition of 10% Pd/C (3 mg). Hydrogen was bubbled into the solution for 10 hrs. After that, the catalyst was filtered off and the solvent was removed in vacuo. The residue was purified by RPHPLC (semipreparative column) using 80% MeOH-H$_2$O to afford [D-Pro⁵] didemnin A. Yield, 2.2 mg (90%); FABMS m/z 943.6 (M+H); $[\alpha]_D^{25} = -72.4$ (c, 0.2, MeOH); R$_f$ 0.62 (CHCl$_3$:MeOH, 19:1), 0.69 (B:A:W, 4:1:5); Anal. Calcd. for C$_{49}$H$_{79}$N$_6$O$_{12}$: M$_r$ 943.5764 (M+H); Found: M$_r$ 943.5746 (M+H) (HRFABMS).

Bioactivity data for several of these compounds is provided in Table II.

TABLE II

| | Inhibition of L1210 cell growth | | |
|---|---|---|---|
| Compounds | ng/mL | Net increase in cells/mL | % I ± S.D. |
| [D-Pro⁵] DA | 300 | 4.7 × 10³ ± 1.2 × 10³ | 99 ± 1 |
| | 100 | 1.8 × 10⁴ ± 2.6 × 10³ | 94 ± 1 |
| | 30 | 1.1 × 10⁵ ± 0 | 66 ± 1 |
| | 10 | 2.0 × 10⁵ ± 5.8 × 10³ | 38 ± 1 |
| | 3 | 2.8 × 10⁵ ± 5.8 × 10³ | 13 ± 7 |
| [D-Thr¹] DA | 3000 | 6.3 × 10³ ± 5.8 × 10² | 98 ± 0 |
| | 1000 | 3.1 × 10⁴ ± 2.1 × 10³ | 90 ± 1 |
| | 300 | 1.4 × 10⁵ ± 1.5 × 10⁴ | 56 ± 8 |
| | 100 | 2.6 × 10⁵ ± 1.2 × 10⁴ | 19 ± 3 |
| [D-MeTyr(Me)⁶] DA | 1000 | 3.4 × 10⁴ | 87 |
| | 300 | 1.4 × 10⁵ | 48 |
| | 100 | 2.2 × 10⁵ | 19 |
| DA | 1000 | ND | — |
| | 100 | 1.4 × 10⁴ | 96 |
| | 10 | 3.1 × 10⁵ | 21 |
| | 1 | 3.5 × 10⁵ | 10 |
| None | 0 | 3.2 × 10⁵ ± 1.0 × 10⁴ | 0 ± 3 |

SYNTHESIS OF [D-MeTyr(Me)⁶] DIDEMNIN A

Z-D-MeLeu-OH

Z-D-Leu (1.32 g, 5 mmol) was dissolved in dry THF (10 ml) and treated with CH$_3$I (7 ml, 50 mmol) and NaH (0.47 g, 20 mmol) at 0° C. The solution was allowed to stir at r.t. for 24 hrs. After that, NaH was destroyed by adding EtOAc and a few drops of water. The clear solution was evaporated to dryness and the residue was dissolved in NaHCO$_3$. The aq. layer was extracted with ether and then acidified to pH 3. The product was extracted into EtOAc and the organic layer washed with water, hypo and finally with water. It was dried over Na$_2$SO$_4$ and evaporated to dryness to give Z-D-MeLeu-OH as an oil; yield 1.3 g, (92%). Anal. Calcd. for C$_{15}$H$_{22}$NO$_4$; M$_r$, 280.1548 (M+H); Found: 280.1549 (HRFABMS).

Z-D-MeLeu-Thr-OTMSe

To a solution of Z-D-MeLeu (0.54 g, 2 mmol) and Thr-OTMSe (0.438 g, 2 mmol) in dry CH$_2$Cl$_2$ (10 ml), N-hydroxysuccinimide (0.230 g, 2 mmol) and EDC (0.382 g, 2 mmol) were added at 0° C. The solution was stirred at 0° C. for 4 hrs. then left in the refrigerator overnight. After that, solvent was evaporated to dryness and the residue was taken up in EtOAc. The organic phase was washed with 5% aq. citric was dried over Na$_2$SO$_4$ and evaporated to dryness. The crude product so obtained was purified on silica gel column using gradient of CHCl$_3$—5% MeOH—CHCl$_3$. Yield 0.3 g, (42%) FABMS m/z 481 (M+H); Anal. Calcd. for C$_{24}$H$_{41}$N$_2$O$_6$Si, M$_r$ 481.2734 (M+H); Found, M$_r$ 481.2734 (M+H) (HRFABMS).

BOC-D-MeTyr(Me)-OH

BOC-D-Tyr (0.7 g, 2.5 mmol) was dissolved in dry THF (5 ml) and treated with CH$_3$Cl (3.56 ml) and NaH (0.3 g) at 0° C. The solution was stirred at r.t. for 20 hrs. After that excess NaH was destroyed by adding EtOAc and few drops of water. The clear solution was evaporated to dryness and residue was dissolved in 5% NaHCO$_3$. It was extracted with EtOAc and then acidified to pH 4 with citric acid. The product was extracted with EtOAc and washed with water, hypo and finally with water. It was dried over Na$_2$SO$_4$ and evaporated to dryness to gel. BOC-D-MeTyr(Me) 0.65 g, (91%); FABMS m/z 310.2 (M+H); Anal. Calcd. for C$_{16}$H$_{24}$NO$_4$, M$_r$ 310.1645 (M+H); Found, M$_r$ 310.1654 (M+H) (HRFABMS).

Z-D-MeLeu-Thr-OTMSe BOC-D-MeTyr(Me)

To the solution Z-D-MeLeu-Thr-OTMSe (0.48 g, 1 mmol) and BOC-D-MeTyr(Me) (0.37 g, 1.2 mmol) in dry CH$_2$Cl$_2$ (12 ml) was added DCC (0.24 g, 1.2 mmol) in presence of DMAP (14 mg) at 0° C. The reaction mixture was stirred at 0° C. for 3 hrs. then left for overnight stirring at r.t. DCU was then filtered off and the filtrate was evaporated to dryness. The residue was taken up in EtOAc and washed with 5% aq. NaHCO$_3$ and water. It was dried over Na$_2$SO$_4$ and evaporated to dryness. The crude product so obtained was purified on silica gel column using gradient of CHCl$_3$—4% MeOH-CHCl$_3$. Yield, 0.7 g, (92%), R$_f$ 0.42 (20% EtOAc-hexane); FABMS 772.4 (M+H); $[\alpha]^{25}_D = +33.1$ (c. 0.3; MeOH); Anal. Calcd. for C$_{40}$H$_{62}$N$_3$O$_{10}$Si, 772.4218 (M+H); Found: 772.4204 (M+H) (HRFABMS).

Z-D-MeLeu-Thr-OTMSe BOC-Isl(T)-Hip-Leu-Pro-D-MeTyr(Me)

BOC-Isl-(TBDMS)-Hip-Leu-Pro-OTMSe (20 mg, 0.023 mmol) was dissolved in dry DMF 0.05 ml and treated with 2M solution of Bu$_4$NF in DMSO (0.05 ml).

The clear solution was left at r.t. for 20 hrs. and was then evaporated and taken up in EtOAc, washed with 5% aq. citric acid, and water. The organic layer was dried over $Na_2SO_4$ and evaporated to dryness.

In another flask Z-D-MeLeu-Thr-OTMSe BOC-D-MeTyr(Me) (12.8 mg) was treated with 6% HCl/dioxane (0.08 ml) to 30 minute at r.t. After that it was evaporated to dryness. It was then treated with the above acid in dry $CH_2Cl_2$ (0.15 ml) in the presence of BOC-Cl (4.5 mg) and $Et_3N$ (0.005 ml) at 0° C. The reaction mixture was stirred at 0° C. for 72 hrs. The reaction was evaporated to dryness and residue was taken up in EtOAc. It was washed with 5% aq. $NaHCO_3$, water, 5% aq. citric acid and finally with water. It was dried and evaporated to dryness. The crude product was purified by preparative silica gel plate using 10% $MeOH-CHCl_3$ as an eluant. Yield 13.3 mg (59.3%): FABMS m/z 109.3 (M+H); $[\alpha]^{25}_D = -37.6°$ (c, 0.2; MeOH). Anal. Calcd. for $C_{37}H_{21}N_6O_{17}Si_2$ $H_2$ 1409.8351 (M+H); Found: $M_r$ 1409.8365 (M+H) (HRFABMS).

Z-[D-MeTyr(Me)$^6$] didemnin A

The protected alicyclic heptapeptide (12 mg) was dissolved in dry THF (0.3 ml) and treated with 2M $Bu_4NF$ in DMSO (0.1 ml). The clear solution was left at r.t. for 20 hrs. It was then evaporated to dryness and residue was taken up in EtOAc, washed with 5% citric acid and finally with water. It was dried over $Na_2SO_4$ and evaporated to dryness. The product was then treated with 4N HCl/dioxane (0.05 ml) for 1 hour at r.t. and was then evaporated and dried in vacuo. The product was subjected to cyclization in dry $CH_2Cl_2$ using DPPA (1.5 µl), DMAP (88 µg) HOBt (1.1 µg) and $Et_3N$ (1.1 µl) at 0° C. The reaction mixture was stirred at 0° C. for 72 hrs. It was then evaporated and residue was taken up in EtOAc. It was washed with 5% $NaHCO_3$, water, 5% aq. citric acid and finally with water. It was then dried over $Na_2SO_4$ and evaporated. The crude material was purified on $C_{18}$ semipreparative column using 85% $MeOH-H_2O$ as an eluant. Yield 3.1 mg (40%) (FABMS m/z 1077.7 (M+H); $[\alpha]_D^{25} = -64.3$ (c., 0.2; MeOH); Anal. Calcd. for $C_{57}H_{85}N_6O_{14}$; $M_r$, 1077.6120 (M+H)/ Found: $M_r$, 1077.6124 (M+H) (HRFABMS).

[D-MeTyr(Me)$^6$] didemnin A

The protected cyclic peptide (3 mg) was subjected to catalytic hydrogenation in MeOH followed by purification by RPHPLC using $C_{18}$ semipreparative column, using 75% $MeOH-H_2O$ as an eluant. Yield, 2.2 mg, (85%); FABMS m/z, 943.6 (M+H), $[\alpha]_D^{25} = -74.6°$ (c, 0.3; MeOH); $R_f$ 0.64 ($CHCl_3$: MeOH, 19.1); Anal. Calcd. for $C_{49}H_{79}N_6O_{12}$: $M_r$ 943.5771 (M+H); Found: $M_r$ 943.5756 (M+H) (HRFABMS).

DEHYDRODIDEMNIN B-TYPE ANALOGUES

Low resolution and high resolution FAB mass spectra were obtained with a VG ZAB-SE or 70 SE 04F mass spectrometers. $^1$HNMR spectra were obtained on Varian XL-200 and GE QE-300 spectrometers. Optical rotations were measured using a Jasco DIP-370 digital polarimeter. HPLC purifications were performed with a Beckman 114M solvent delivery pump system, Isco V$^4$ variable wavelength absorbance detector and a Linear 1200 chart recorder. The HPLC column was a C18 10µ semipreparative Altech (10 mm×25 cm). Compounds were judged to be pure on the basis of silica gel TLC using the following solvent systems: EtOAc:Hexane; 1:2 (A), n-BuOH:AcOH:Water:4:1:5 (B), $CHCl_3$:MeOH:AcOH; 19:1:0.5 (C) and $CH_2Cl_2$ EtOAc; 2:3 (D). Injection of the final dehydrodidemnin analogue on the above reversed phase HPLC column indicated compounds of greater than 98% purity.

Phepyruv-Pro-OBn (I)

A solution of phenylpyruvic acid (1.64 g, 10 mmol) and Pro-OBn.hydrochloride (2.41 g, 10 mmol) were dissolved in dry $CH_2Cl_2$ (10 ml) and dry DMF (5 ml) was chilled to 0° C. and N-methylmorpholine (1.12 ml, 10 mmol) was added with stirring, followed by HOBt (1.53 g, 10 mmol) and DCC (2.06 g, 10 mmol). The reaction mixture was stirred at 0° C. for 2 hr., then at room temperature (r.t.) overnight. DCU was filtered off and the solvent was evaporated to dryness. The residue was taken up in EtOAc and washed successively with 5% aq. citric acid, water, 5% aq. $NaHCO_3$ and water. The organic layer was then dried over $Na_2SO_4$ and evaporated to dryness. The crude material was purified on a silica gel column using EtOAc-hexane (1:2) as an eluant, yield 3.0 g (86%), $R_f$ 0.52 (A), 0.61 (B); $[\alpha]_D = -65.9°$ (c, 0.4, MeOH), FABMS:m/z 352.1 (M+H), Anal. Calcd. for $C_{21}H_{22}NO_4$: $M_r$, 352.153 (M+H). Found: $M_r$, 352.1549 (HRFABMS).

-Ketobutyryl-Pro-OBn (II)

-Ketobutyric acid (0.6 g, 5.9 mmol) was coupled with Pro-OBn (1.2 g, 4.9 mmol) using the DCC/HOBt procedure in the manner described for compound I; yield 1.29 g (90%), $R_f$ 0.49 (A), 0.53 (B), $[\alpha]_D$ −69.5° (c, 0.3, MeOH), FABMS: m/z 290.1(M=H), Anal. Calcd. for $C_{16}H_{20}NO_4$: $M_r$, 290.1387(M+H). Found $M_r$, 290.1382 (HRFA8MS).

Pyruv-Azt-OBn (III)

Pyruvic acid (0.69 g, 7.9 mmol) was coupled with PTSA.Azt-OBn (1.5 g, 3.9 mmol) using DCC/HOBt procedure in the manner described for I, yield: 0.82 g (80%), $R_f$ 0.32 (A), 0.38 (B), $[\alpha]_D = -69.1°$ (c, 0.37, MeOH), FABMS: m/z 262.1 (M+H), Anal. Calcd. for $C_{14}H_{15}NO_4$: $M_r$, 262.1077(M+H). Found: $M_r$, 262.1079 (HRFABMS).

Pyruv-Sar-OBn (IV)

Pyruvic acid (0.81 g, 4.6 mmol) was coupled with PTSA.Sar-OBn (1 g, 4.6 mmol) using DCC/HOBt procedure exactly in a manner described for compound I. Yield: 0.92 g (80%), $R_f$ 0.5 (A) and 0.55 (B), FABMS: m/z 250.1 (M+H), Anal. Calcd. for $C_{13}H_{16}NO_4$: $M_r$, 250.1080 (M+H). Found: $M_r$, 250.1079 (M+H) (HRFABMS).

Pyruv-D-Pro-OBn (V)

Pyruvic acid (0.75 g, 8.6 mmol) was coupled with PTSA.D-Pro-OBn (0.92 g, 4.3 mmol) using DCC/HOBt procedure exactly in a manner described for compound I. Yield 0.89 g (85%), $R_f$ 0.39 (A) and 0.44 (B), FABMS m/z 276.1 (M+H); $[\alpha]_D = 65.1$ (c, 0.2; MeOH), Anal Calcd. for $C_{15}H_{18}NO_4$: $M_r$, 276.1233 (M+H). Found: $M_r$, 276.123 (M+H) (HRFABMS).

Pyruv-Pip-OBn (VI)

Pyruvic acid (0.22 g, 2.54 mmol) was coupled with PTSA.Pip-OBn (0.5 g, 1.27 mmol) in using DCC/HOBt procedure exactly in manner described for Compound I. Yield: 0.29 g (80%), $R_f$ 0.6 (A) and 0.64 (B), FABMS: m/z 290.1 (M+H), $[\alpha]_D = -72.4$ (c, 0.6.; MeOH), Anal.

Calcd. for $C_{16}H_{20}N_4$: $M_r$, 290.1385 (M+H). Found: $M_r$, 290.1378 (M+H) (HRFABMS).

Pyruv-Acc-OBn (VII)

Pyruvic acid (0.46 g, 5.29 mmol) was coupled with PTSA.Acc5-OBn (1.38 g, 3.5 mmol) using DDC/HOBt procedure exactly in a manner described for compound I. Yield: 0.73 g (80%), $R_f$ 0.71 (A) and 0.78 (B), FABMS: m/z 290.1 (M+H), Anal. Calcd. for $C_{16}H_{20}NO_4$: $M_r$, 290.1385 (M+H). Found: $M_r$, 290.1392 (M+H) (HRFABMS).

Phepyruv-Pro (VIII)

Compound VII (1 g, 2.8 mmol) was dissolved in EtOAc (30 ml) followed by addition of 10% Pd/C under inert atmosphere. Hydrogen was bubbled under vigorous stirring. After the completion of the reaction as monitored by TLC, catalyst was filtered off and filtrate was evaporated to dryness in vacuo, to provide Phepyruv-Pro as an oil. Yield: 0.7 g (94%), $R_f$ 0.48 (C) and 0.53 (B), $[\alpha]_D = -48.1$ (c, 1.4; MeOH), FABMS: m/z 262.1 (M+H).

-ketobutyryl-ProOH (IX)

This compound was obtained from compound II (I g, 3.4 mmol) exactly in a manner described for compound VIII. Yield: 0.64 g (93%), $R_f$ 0.41 (C) and 0.45 (B), FABMS: m/z 200 (M+H), $[\alpha]_D = -86.6$ (c, 0.7; MeOH), Anal. Calcd. for $C_9H_{14}NO_4$: $M_r$, 200.0927 (M+H). Found: $M_r$, 200.0923 (M+H) (HRFABMS).

Pyruv-Azt-OH (X)

This compound was obtained from compound III (0.4 g, 2.3 mmol) in the manner described for compound VIII, yield: 0.23 g (90%), $R_f$ 0.29 (C), 0.32 (B), $[\alpha]_D = -98.1°$ (c, 0.11, MeOH), FABMS: m/z 172 (M+H), Anal. Calcd. for $C_7H_{10}NO_4$: $M_r$, 172.0609 (M+H). Found: $M_r$, 172.0605 (HRFABMS).

Pyruv-Sar-OH (XI)

This compound was obtained from compound IV (0.6 g, 2.4 mmol) in the manner described for compound VIII, yield: 0.34 g (90%), $R_f$ 0.45 (C), 0.5 (B), FABMS: m/z 160.0 (M+H), Anal. Calcd. for $C_6H_{10}NO_4$: $M_r$, 160.0612 (M+H). Found: $M_r$, 160.0610 (HRFABMS).

Pyruv-D-Pro-OH (XII)

This compound was obtained from compound V (0.8 g, 2.9 mmol) in the manner described for compound VIII, yield: 0.53 g (93%), $R_f$ 0.32 (C), 0.38 (B), $[\alpha]_D = 72.5°$ (c, 1.3, MeOH), FABMS: m/z 186 (M+H); Anal. Calcd. for $C_8H_{12}NO_4$: $M_r$, 186.0762(M+H). Found: $M_r$, 186.0758 (HRFABMS).

Pyruv-Pip-OH (XIII)

This compound was obtained from compound VI (0.28 g, 0.96 mmol) in the manner described for compound VIII, yield: 0.17 g (92%), $R_f$ 0.52 (B), $[\alpha]_D = -85.1$ (c, 0.5; MeOH), FABMS: m/z 200 (M+H), Anal. Calcd. for $C_9H_{14}NO_4$: $M_r$, 200.0927 (M+H). Found: $M_r$, 200.0923 (HRFABMS).

Pyruv-Acc⁵-OH (XIV)

This compound was obtained from compound VII (0.28 g, 0.96 mmol) in the manner described for compound VIII, yield: 0.17 g (90%), $R_f$ 0.58 (C), 0.62 (B), FABMS: m/z 200.1 (M+H), Anal. Calcd. for $C_9H_{14}NO_4$: $M_r$, 200.0929 (M+H). Found: $M_r$, 200.0923 (HRFABMS).

PhePyruv-Pro Didemnin A (XV)

Phenylpyruvic acid (0.166 g, 0.63 mmol) was dissolved in dry $CH_2Cl_2$ (2 ml) and cooled to 10° C. To this EDC (0.061 g, 0.31 mmol) was added under stirring. The clear solution was stirred at 10° C. for 1.5 hr. After that didemnin A (0.03 g, 0.031 mmol) was added and the reaction mixture was stirred at 10° C. for 2 hrs. It was then left in refrigerator overnight. Next DMAP (5 mg) was added and the reaction mixture was left again in the refrigerator for 20 h. After that another batch of preactivated phenylpyruvic acid (0.83 g, 0.31 mmol) with EDC (0.030 g, 0.15 mmol) was added to the reaction mixture. The reaction mixture was left 0° C. for another 24h. After that the solvent was evaporated and residue taken up in EtOAc, washed With 5% aq. $NaHCO_3$ and water. The organic layer was dried over $Na_2SO_4$ and evaporated to dryness. The crude material was purified on silica gel column using $CH_2Cl_2$-EtOAc; 2:3 as an eluant. It was further purified to 96% homogeneity on RP HPLC using 85% MeOH-$H_2O$. Yield: 31.7 mg (85%), $R_f$ 0.43 (D), 0.53 (B), $[\alpha]_D = -63.3°$ (c, 0.36, MeOH), FABMS: m/z 1186.6 (M+H), Anal. Calcd. for $C_{63}H_{92}N_7O_{15}$: $M_r$, 1186.6656 (M+H). Found: $M_r$, 1186.6651 (HRFABMS).

-Ketobutyryl-Pro Didemnin A (XVI)

This compound was synthesized in the manner described for compound XV, yield: 29 mg (82%), $R_f$ 0.39 (D), 0.48 (B), $[\alpha]_D = -93.2°$ (c, 1.6, MeOH), FABMS: m/z 1124.6 (M+H), Anal. Calcd. for $C_{58}H_{90}N_7O_{15}$: $M_r$, 1124.6481 (M+H). Found: $M_r$, 1124.6467 (HRFABMS).

Pyruv-Azt Didemnin A (XVII)

This compound was synthesized in the manner described for compound XV, yield: 27 mg (78%), $R_f$ 0.24 (D), 0.32 (B), $[\alpha]_D = -103.3$ (c, 1.6, MeOH), FABMS: m/z 1096 (M+H), Anal. Calcd. for $C_{56}H_{86}N_7O_{15}$: $M_r$, 1096.6174 (M+H). Found: $M_r$, 1096.6266 (HRFABMS).

Pyruv-Sar Didemnin A (XVIII)

To a chilled solution of compound XI (0.02 g, 0.12 mmol) in dry $CH_2Cl_2$ (2 ml), N-hydroxysuccinimide (0.014 g, 0.12 mmol) and DCC (0.026 g, 0.12 mmol) were added under stirring. The reaction was stirred at 0° C. for 10 hrs. After that didemnin A (0.03 g, 0.031 mmol) was added and reaction mixture as allowed to stir at r.t. for 4 days. The DCU was filtered off and filtrate was evaporated to dryness. The residue was taken up in EtOAc, washed with 5% aq. $NaHCO_3$ and water. It was than dried over $Na_2SO_4$ and evaporated to dryness. The crude product was subjected to purification on silica gel column using $CH_2Cl_2$OEtOAc; 2:3 as an eluant. It was further purified to more than 97% homogeneity on RP HPLC using 5% MeOH-$H_2O$ as mobile phase. Yield: 21 mg (62%), $R_f$, 0.4 (D), 0.49 (B), $[\alpha]_D = -69.2°$ (c, 1.1, MeOH), FABMS: m/z 1084.6 (M+H); Anal. Calcd. for $C_{55}H_{87}N_7O_{15}$: $M_r$, 1084.6186 (M+H). Found: $M_r$, 1084.6182 (HRFABMS).

Pyruv-D-Pro Didemnin A (XIX)

This compound was synthesized in the manner described for compound XV, yield: 18.3 mg (52%), $R_f$, 0.31 (D), 0.39 (B), $[\alpha]_D = -27.6°$ (c, 0.7, MeOH), FABMS: m/z 1110.6 (M+H), Anal. Calcd. for $C_{57}H_{88}N_7O_{15}$: $M_n$ 1110.6355 (M+H). Found: $M_n$ 1110.6338 (HRFABMS).

The cytotoxic activity (inhibition of L1210 cell growth) of the DDB analogues (Compounds XV-XIX, above) is shown in Table III and is expressed as percentage inhibition (%I). The results have been compared with Didemnin B (DB) and dehydrodidemnin B (DDB). As evident from the results shown in Table III, all of the analogues exhibited cytotoxic activity in a dose dependent manner.

TABLE III

| Inhibition of L1210 cell growth by DDB analogues | | | |
|---|---|---|---|
| Compound | | Net increase in cells/mL | % I |
| Phepyruv-Pro-DA | 30 | $1.1 \times 10^4$ | 97 |
| | 10 | $5.3 \times 10^4$ | 85 |
| | 3 | $2.0 \times 10^5$ | 44 |
| | 1 | $3.5 \times 10^5$ | 3 |
| α-Ketobutyryl-Pro-DA | 10 | 0 | 100 |
| | 3 | 0 | 100 |
| | 1 | $2.3 \times 10^4$ | 94 |
| | 0.3 | $2.5 \times 10^5$ | 31 |
| | 0.1 | $3.9 \times 10^5$ | −8 |
| Pyruv-Azt-DA | 10 | 0 | 100 |
| | 3 | 0 | 100 |
| | 1 | $2.5 \times 10^4$ | 93 |
| | 0.3 | $2.8 \times 10^5$ | 22 |
| | 0.1 | $4.1 \times 10^5$ | 14 |
| Pyruv-D-Pro-DA | 100 | 0 | 100 |
| | 30 | $7.0 \times 10^3$ | 98 |
| | 10 | $9.5 \times 10^4$ | 74 |
| | 3 | $3.3 \times 10^5$ | 8 |
| Pyruv-Sar-DA | 100 | 0 | 100 |
| | 30 | 0 | 100 |
| | 10 | $9.0 \times 10^3$ | 98 |
| | 3 | $7.4 \times 10^4$ | 79 |
| | 1 | $2.3 \times 10^5$ | 36 |
| DB | 3 | $1.2 \times 10^4$ | 98 |
| | 1 | $1.2 \times 10^5$ | 76 |
| | 0.3 | $3.9 \times 10^5$ | 24 |
| DDB | 3 | $3.7 \times 10^3$ | 99 |
| | 1 | $1.6 \times 10^4$ | 97 |
| | 0.3 | $1.6 \times 10^5$ | 69 |
| | 0.1 | $4.4 \times 10^5$ | 14 |
| None | 0 | $5.1 \times 10^5$ | 0 |

As shown in Table III, at 3 ng/ml analogues VI and XVII retained the full cytotoxicity of DDB whereas analogues XV and XIX were found to be only partially active. Analogue XVIII having D-Pro at position 8 although exhibiting full cytotoxicity at higher concentration such as 100 ng/ml, at lower concentrations turned out to be completely inactive. At 1 ng/ml, however, cytotoxicity of only compounds XVI and XVII were comparable to that of DDB, the rest of the congeners being inactive.

The IC$_{50}$ values (see Table IV) for Compounds XVI and XVII were found to be 0.4 and 0.6 respectively, very close to the value of 0.2 for DDB. These results clearly suggest that pyruvic acid at position 9 and L-proline with a 5-membered pyrrolidone ring at position 8 are very important structural features of DDB, required for very high order of cytotoxic activity against L1210 cells.

| IC$_{50}$ values of DDB analogues for L1210 cells | |
|---|---|
| Compounds | IC$_{50}$ |
| Phepyruv-Pro-DA | 3.5 |
| α-Ketobutyryl-Pro-DA | 0.4 |
| Pyruv-Azt-DA | 0.6 |
| Pyruv-D-Pro-DA | 6 |
| Pyruv-Sar-DA | 1 |

| IC$_{50}$ values of DDB analogues for L1210 cells | |
|---|---|
| Compounds | IC$_{50}$ |
| -continued | |
| DDB | 0.2 |
| DB | 0.5 |

The antiviral activity of DDB congeners (Compounds XV-XIX) are shown in Table V and expressed as percentage of inhibition in plaque formation. Except for Compound XV, all analogues exhibited antiviral activity against VSV in a dose dependent manner. The interesting feature of the congeners synthesized is that they exhibited very low order of activity against HSV-1 in contrast to DDB which exhibited high order of antiviral against both VSV and HSV-1.

TABLE V

| Anti VSV and HSV-1 Activity of DDB analogues | | | | | |
|---|---|---|---|---|---|
| Compounds | μg/mL | BHK | VSV | CV-1 | HSV |
| Phepyruv-Pro-DA | 3 | 16 | ? | 12 | − |
| | 1 | 13 | − | 10 | − |
| | 0.3 | 12 | − | 5 | − |
| | 0.1 | 10 | − | 0 | − |
| α-Ketobutyryl-Pro-DA | 3 | 0 (PT)$^a$ | +++ | 0 (LS)$^b$ | ? |
| | 1 | 0 (PT) | ++ | 0 (LS) | ± |
| | 0.3 | 0 (PT) | ++ | 5 | ± |
| | 0.1 | 0 (PT) | + | 0 | − |
| | 0.03 | 0 (PT) | ± | ND$^c$ | ND |
| | 0.01 | 0 | − | ND | ND |
| Pyruv-Azt-DA | 3 | 0 (PT) | +++ | 0 (LS) | ? |
| | 1 | 0 (PT) | ++ | 0 (LS) | ± |
| | 0.3 | 0 (PT) | ++ | 5 | ± |
| | 0.1 | 0 (PT) | + | 0 | − |
| | 0.03 | 0 (PT) | ± | ND | ND |
| | 0.01 | 0 | − | ND | ND |
| Pyruv-D-Pro-DA | 3 | 0 (PT) | +++ | 0 (LS) | ± |
| | 1 | 0 (PT) | +++ | 0 | ± |
| | 0.3 | 0 (PT) | + | 0 | − |
| | 0.1 | 0 (PT) | ± | 0 | − |
| | 0.03 | 0 (PT) | − | ND | ND |
| | 0.01 | 0 | − | ND | ND |
| Pyruv-Sar-DA | 3 | 0 (PT) | +++ | 0 (LS) | ? |
| | 1 | 0 (PT) | +++ | 0 (LS) | ± |
| | 0.3 | 0 (PT) | ++ | 0 | − |
| | 0.1 | 0 (PT) | ± | 0 | − |
| | 0.03 | 0 | − | ND | ND |
| | 0.01 | 0 | − | ND | ND |
| DDB | 1 | 0 (PT) | +++ | 0 (LS) | +++ |
| | 0.3 | ND | ND | 0 (LS) | ++ |
| | 0.1 | 0 (PT) | ± | 0 | ± |

$^a$PT, Partial toxicity.
$^b$LS, Lightly stained cell sheet.
$^c$ND, Not determined Surprisingly the biological activity profile of all the congeners except Compound XV against VSV remained more or less similar to that of DDB. The DDB congeners along with DDB were also screened against VIV (see, Table VI) and they were found to be completely inactive, thereby suggesting selectivity of the congeners against RNA virus.

TABLE VI

| Anti Viv Activity Of DDB Analogues | | | |
|---|---|---|---|
| Compounds | | % Protection | % Cytotoxicity |
| Phepyruv-Pro-DA | 10 | ND$^a$ | ND |
| | 3 | ND | ND |
| | 1 | I$^b$ | 88 |
| | 0.3 | I | 57 |
| α-Ketobutyryl-Pro-DA | 10 | ND | ND |
| | 3 | ND | ND |
| | 1 | ND | ND |
| | 0.3 | I | 87 |
| Pyruv-Azt-DA | 10 | ND | ND |

TABLE VI-continued
Anti Viv Activity Of DDB Analogues

| Compounds | | % Protection | % Cytotoxicity |
|---|---|---|---|
| | 3 | ND | ND |
| | 1 | ND | ND |
| | 0.3 | I | 77 |
| Pyruv-D-Pro-DA | 10 | ND | ND |
| | 3 | I | 76 |
| | 1 | I | 57 |
| | 0.3 | 60 | 29 |
| Pyruv-Sar-DA | 10 | ND | ND |
| | 3 | ND | ND |
| | 1 | I | 76 |
| | 0.3 | I | 50 |
| AZT | 30 (uM) | 72 | 14 |
| | 10 | 58 | 11 |
| | 3 | 26 | 7 |
| | 1 | 10 | 5 |
| | 0 | 0 | 0 |
| DDB | 30 | ND | 93 |
| | 10 | ND | 81 |
| | 3 | −71 | 34 |
| | 1 | −20 | 11 |
| | 0.3 | 8 | 3 |

[a]ND, Not determined
[b]I, indeterminate

Isolation of Didemnins M (12) and N (13), Nordidemnin N (14), Epididemnin A (15), and Acyclodidemnin A (16)

The source material for these didemnins (see, Scheme I, for structures) was a methylene chloride extract of 500 Kg of the tunicate *T. solidum* obtained from the Upjohn Company (which was produced during preparation of didemnin B for phase II clinical trials), and where it had been stored in a freezer for two years.

A portion (2 L) of the $CH_2Cl_2$ solution was used for the present invention. A solvent partition of the solid (32 g) obtained from evaporation of the methylene chloride solution (0.5 L) gave 16 g of relatively polar peptide-rich Fraction B which was separated by a gravity silica gel column into 12 fractions (Scheme II).

SCHEME I

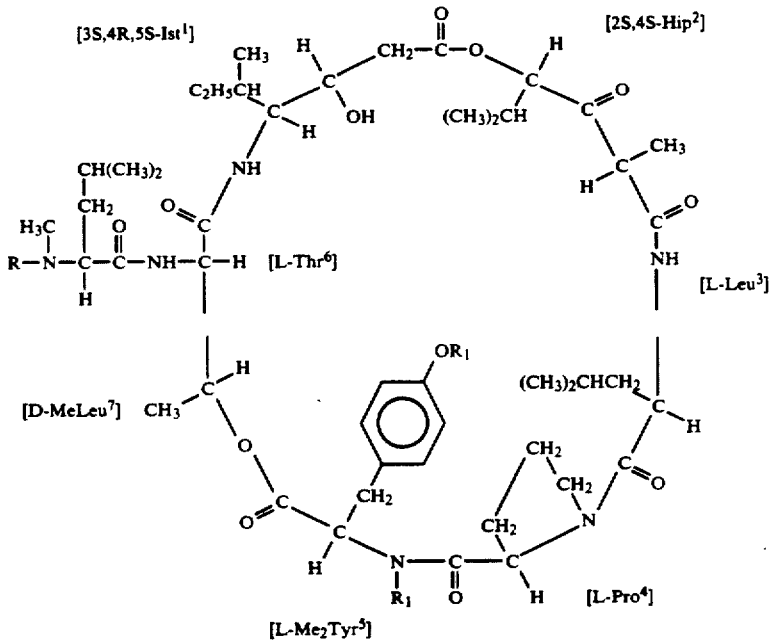

didemnin X (10): R = Hydec-(L-Gln)₃-L-Lac-L-Pro-, R₁ = CH₃
didemnin Y (11): R = Hydec-(L-Gln)₄-L-Lac-L-Pro-, R₁ = CH₃
didemnin M (18): R = L-pGlu-L-Gln-L-Lac-L-Pro, R₁ = CH₃
didemnin N (13): R = L-Lac-L-Pro-, R₁ = H
nor didemnin N (14): = [Norsta¹]didemnin N
epididemnin A (15) = [4-epiHip²]didemnin A

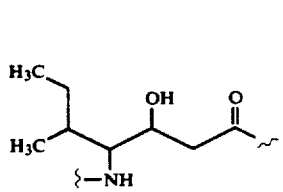

isostatine: Ist

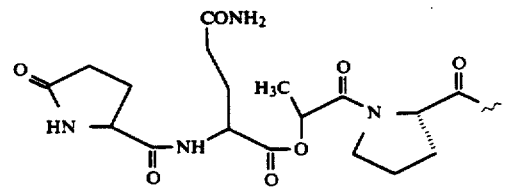

L-pGlu-L-Gln-O-L-Lac-L-Pro-

SCHEME I

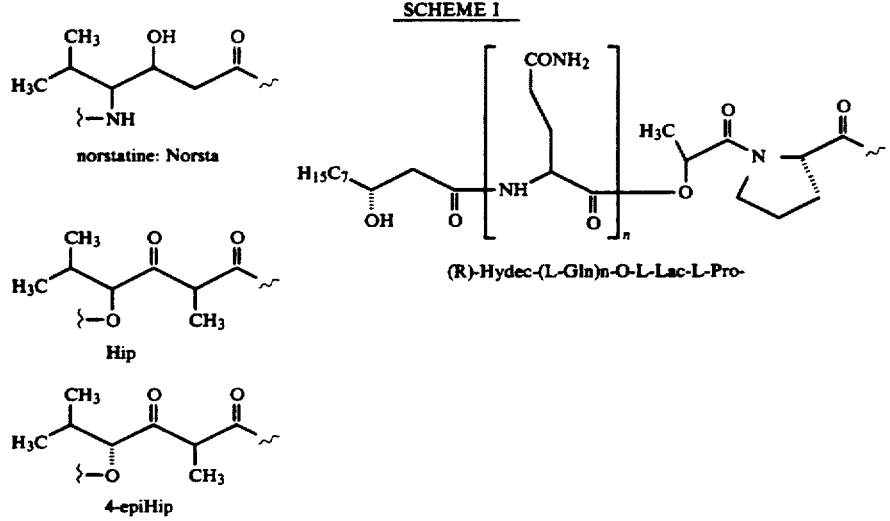

norstatine: Norsta

Hip 4-epiHip (R)-Hydec-(L-Gln)n-O-L-Lac-L-Pro-

SCHEME II

Upjohn Extract (CH$_2$Cl$_2$ solution, (a) 0.5 (b) 1.5 L)

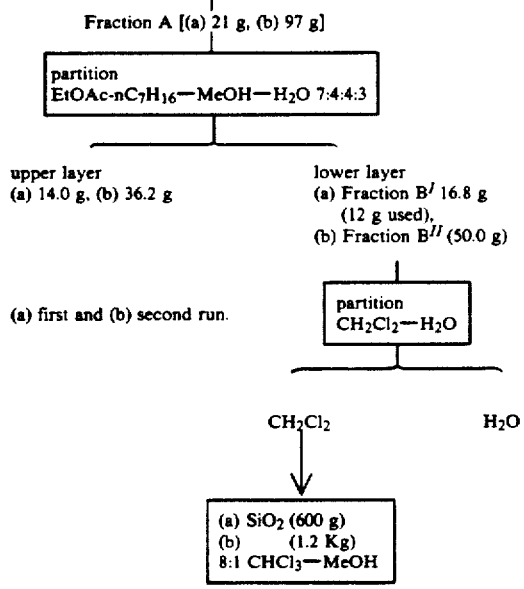

An additional amount of the solid (96 g) was obtained from 1.5 L of the methylene chloride solution which was processed as above and separated by a gravity silica gel column into 13 fractions; and a FAB mass spectra of each fraction was obtained (see, Scheme III, and Table 7).

TABLE 7

FABMS Data for the Fractions Obtained From Silica Gel Separation of Fraction B$^I$ (a) and B$^{II}$ (b)

| Fr # | Weight (a)[b] | Fr # | Weight (b)[b] | FABMS data for separation (b)[a] m/z |
|---|---|---|---|---|
| B$^I$-1 | 48 (mg) | B$^{II}$-1 | 0.3 (g) | NT |
| 2 | 238 | 2 | 4.19 | 1112 (B) |
| 3 | 346 | 3 | 2.25 | 1113 (B), 1099 (nor B) |
| 4 | 492 | 4 | 1.05 | NT[c] |
| 5 | 629 | 5 | 0.93 | 944 (A) |
| 6 | 605 | 6 | 2.23 | 944 (A) |
| 7 | 5690 | 7 | 4.26 | 943 (A), 1094 (new), 1668 (X) |

TABLE 7-continued

FABMS Data for the Fractions Obtained From Silica Gel Separation of Fraction B$^I$ (a) and B$^{II}$ (b)

| Fr # | Weight (a)[b] | Fr # | Weight (b)[b] | FABMS data for separation (b)[a] m/z |
|---|---|---|---|---|
| 8 | 763 | 8 | 4.49 | 943 (A), 1480 (E), 1667 (X) |
| 9 | 525 | 9 | 8.37 | 944 (A), 1096 (new), 1481 (E), 1668 (X), |
| 10 | 414 | 10 | 3.38 | 929 (nor A), 1480 (E). |
| 11 | 955 | 11 | 2.44 | 929 (nor A), 1480 (E) |
| 12 | 309 | 12 | 2.16 | 929, (nor A), 961 (acyclo A), 1466 (nor E)[d], 1794 (Y) |
| 13 | | 13 | 11.13 | (1:1 methanol-CHCl$_3$ wash. Mostly didemnin D) |

[a]The most reasonable assignments in ( ) for the molecular ions. NT = not taken.
[b](a) first and (b) second run.
[c]This fraction contained didemnins M, N, norN.
[d]Not purified.

SCHEME III

Fraction 5 (270 mg, see Table 7 (a))

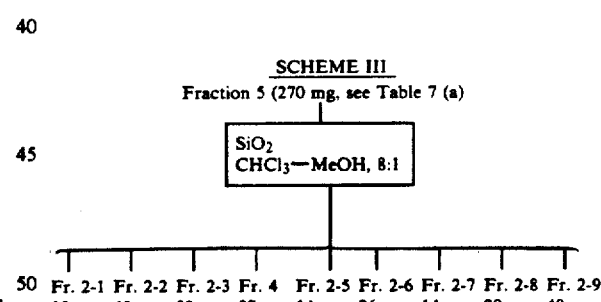

Fr. 2-1  Fr. 2-2  Fr. 2-3  Fr. 4  Fr. 2-5  Fr. 2-6  Fr. 2-7  Fr. 2-8  Fr. 2-9
15 mg   48 mg   32 mg   27 mg  14 mg   26 mg   14 mg   20 mg   49 mg

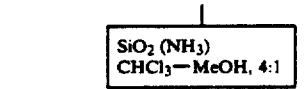

passed      absorbed (pigments)

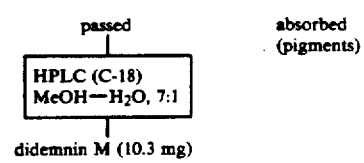

didemnin M (10.3 mg)

The fractions containing new peptides were further separated by silica gel column or CCC. Further chromatographic purification using a silica gel, Sephadex LH-20 and reversed-phase HPLC afforded new didemnins M (12) (Scheme III), and N (13), nordidemnin N (14), epididemnin A (15), acyclodidemnin A (16, and isodidemnin A₁ (1a) (Scheme IV).

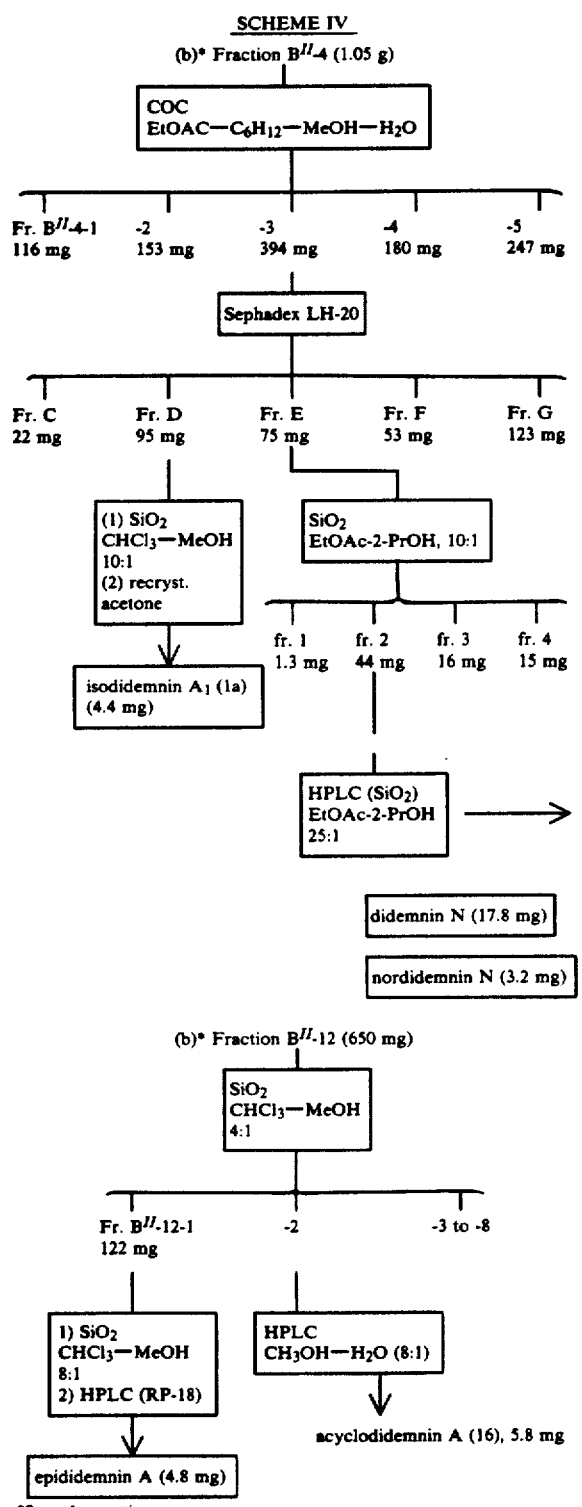

Structure of Didemnin M (Compound 12)

The molecular formula of didemnin M (Compound 12) was deduced to be $C_{67}H_{102}N_{10}O_{19}$ based on high resolution fast atom bombardment mass spectroscopic (HRFABMS) data (1351.1791, 0.9 mmu, M+H). The $^1$H NMR spectrum of Compound 12 resembled that of didemnin B, suggesting that they were related. The $^{13}$C NMR spectrum of Compound 12 counted a total of 66 carbons, and 12 amide carbonyl peaks were observed between 168 and 178 ppm. The FABMS fragmentation pattern for the side chain, and HRMS data on each fragmentation ion established the sequence pGlu-Gln-Lac-Pro-MeLeu-.

A comparison of the chiral GC analysis of the derivatized acid hydrolyzate of Compound 12 with that of didemnin E showed the amino acid components of those compounds to be the same. Treatment of Compound 12 with I-I-[bis(trifluoroacetyl)]iodobenzene followed by GC analysis assigned an alpha linkage to the Gln unit in Compound 12 as in Compound 10 and Compound 11. Thus, the structure of 12 was determined as L-pGlu-L-Gln-didemnin B.

Structures of Didemnin N (13) and Nordidemnin N (14)

The HRFABMS data for didemnin N (Compound 13) on the protonated molecular ion at m/z 1084 agreed with a molecular formula of $C_{55}H_{58}N_7O_{15}$(M+H, 0.5 mmu). The $^1$H and $^{13}$C NMR spectra of Compound 13 were similar to those of didemnin 8 (Compound 17), except for the lack of two methyl signals and the presence of a new amide signal at 6.06 ppm. Chiral GC analysis of the hydrolyzate of 13 showed the presence of L-Tyr instead of L-Me₂Tyr in Compound 13, but all other peaks were the same as those of Compound 17. Sequences of Compound 13 were shown to be the same as those of Compound 17 by FABMS/MS analysis. Almost every important fragmentation ions for Compound 13 appeared parallel to those of Compound 17, but differing by 28 mu if the fragment contained tyrosine instead of Me₂Tyr.

Nordidemnin N (Compound 14) showed $^1$H NMR characteristics similar to those of Compound 13, but the molecular weight of Compound 14 (1070.5996, M+H) which agreed with a protonated molecular formula of $C_{54}H_{84}N_7O_{15}$, was 14 mu smaller than Compound 13. A comparison of GC data for the derivatized acid hydrolyzate of Compound 14 with those for nordidemnin B showed the presence of a Norsta residue in Compound 14. It also showed small peaks for Ist due to an impurity of Compound 13 in the sample of Compound 14. FABMS/MS of Compound 14 showed fragmentation ions almost parallel to those of Compound 13 but differing by 14 mu if the fragment contain the Norsta unit. These data constructed the same sequence in Compound 14 as in Compound 13.

These data assigned structures of didemnin N (Compound 13) and nordidemnin N (Compound 14) to be [Tyr⁵]didemnin B and [Tyr⁵]nordidemnin B, respectively. The configurations of the Hip, MeLeu and Lac unit were remained undetermined since their enantiomers were not separated by the chiral GC used.

Although the didemnins possess three pharmacologically important properties, antiviral, antitumor and immunosuppressive activities, it has been found that those activities are occasionally accompanied by undesired toxicities. Thus, one goal of this invention was the design of more selective didemnin analogues.

Modification of didemnins in this embodiment of the invention involved a modification of the cyclic hexapeptide ring component.

Preliminary modifications of polar functional groups on the ring portion such as the keto group in Hip and the hydroxyl group in Ist were first conducted by Gloer, J. B., Ph. D. Dissertation, University of Illinois, Urbana; 1983. *Chem. Abstr.*, 1983, 103, 122692b; *Diss. Abstr. Int. B.*, 1983, 45, 188-189. [Dihydro(2S,3S,4S)-Hip[2]]didemnin A (Compound 20) and N,O-diacetyldidemnin A (Compound 32) showed weaker cytotoxicity than Compound 1; however, in the case of Compound 32, an improvement of the antiviral activity (in vitro) was observed. (See, Rinehart, K. L., et al., *J. Nat. Prod.*, 1988, 51, 1-21).

Isostatine analogs were synthesized and incorporated into didemnins and their cytotoxicity was measured. [(3S, 4R)-Sta[1]]-didemnin A (Compound 58), [(3R, 4R, 5S)Ist[1]]didemnin A (Compound 59), [(3S, 4R, 5R)-Ist[1]]didemnin A (Compound 60), and [(3S, 4S, 5S)-Ist[1]]didemnin A (Compound 61), however, had lost cytotoxicity.

In the present embodiment of the invention, a new analog O-acetyldidemnin A (Compound 114), was prepared through protection of the N-terminus of Compound 1 with a benzyloxycarbonyl (Z) group followed by O-acetylation and deprotection. As a by-product of the catalytic hydrogenation in the deprotection reaction, [O-acetylIst[1]dihydroHip[2]]didemnin A (Compound 97) was obtained, which may also be a probe of the importance of the keto group in the Hip residue. A by-product of the Mitsunobu reaction, Compound 83, has the anhydroIst group. This compound may indicate the importance of the hydroxyl group in Ist and of the effect on bioactivites of olefinic carbons introduced into the macrocyclic peptide backbone.

[HexahydroMe$_2$Tyr[5]]didemnins A (Compound 115) and B (Compound 116) and [N-methyl-hexahydophenylalanyl[5]] didemnins A (Compound 117) and B (Compound 118) were obtained as reduction products of didemnins A or B, respectively, when platinum on activated carbon was used in the catalytic hydrogenation reaction under ambient conditions.

Sequences of all didemnins prepared in this embodiment of the invention are summarized below in Table 8.

TABLE 8

| Compound | Origin[a] | Subunits[b] | | | | | | | | | | | | | |
|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 |
| Didemnin A Class | | | | | | | | | | | | | | | |
| Didemnin A (1) | N | Ist | Hip | Leu | Pro | Me$_2$Tyr | Thr | D-MeLeu | H | | | | | | |
| Nordidemnin A (21) | N | Norst | Hip | Leu | Pro | Me$_2$Tyr | Thr | D-MeLeu | H | | | | | | |
| Epididemnin A (15) | N | Ist | 4RHip | Leu | Pro | Me$_2$Tyr | Thr | D-MeLeu | H | | | | | | |
| Isodidemnin A (1a) | N | Ist | Hip | Leu | Pro | Me$_2$Tyr | Thr | D-MeLeu | H | | | | | | |
| O-Acetyldidemnin A (114) | S | Ist (OAc) | Hip | Leu | Pro | Me$_2$Tyr | Thr | D-MeLeu | H | | | | | | |
| N-Acetyldidemnin A (54) | S | Ist | Hip | Leu | Pro | Me$_2$Tyr | Thr | D-MeLeu | Ac | | | | | | |
| Diacetyldidemnin A (32) | S | Ist (OAc) | Hip | Leu | Pro | Me$_2$Tyr | Thr | D-MeLeu | Ac | | | | | | |
| N-Propionyldidemnin A (98) | S | Ist | Hip | Leu | Pro | Me$_2$Tyr | Thr | D-MeLeu | nCOC$_2$H$_5$ | | | | | | |
| N-(L-Leu)didemnin A (99) | S | Ist | Hip | Leu | Pro | Me$_2$Tyr | Thr | D-MeLeu | Leu | | | | | | |
| N-(D-Pro)didemnin A (101) | S | Ist | Hip | Leu | Pro | Me$_2$Tyr | Thr | D-MeLeu | D-Pro | | | | | | |
| N-(L-Pro)didemnin A (100) | S | Ist | Hip | Leu | Pro | Me$_2$Tyr | Thr | D-MeLeu | Pro | | | | | | |
| N-(Honsu)didemnin A (111) | S | Ist | Hip | Leu | Pro | Me$_2$Tyr | Thr | D-MeLeu | Hor | | | | | | |
| [H$_6$—Me$_2$Tyr$^5$]didemnin A (115) | S | Ist | Hip | Leu | Pro | H$_6$Me$_2$Tyr | Thr | D-MeLeu | H | | | | | | |
| [H$_6$—MePhe$^5$]didemnin A (117) | S | Ist | Hip | Leu | Pro | H$_6$MePhe | Thr | D-MeLeu | H | | | | | | |
| Acyclodidemnin A (16) | S | Ist | Hip | Leu | Pro | HOMe$_2$Tyr | ThrOH | D-MeLeu | H | | | | | | |
| [H$_2$-(2S,3R,4S)Hip$^2$]didemnin A (84) | S | Ist | H$_2$Hip | Leu | Pro | Me$_2$Tyr | Thr | D-MeLeu | H | | | | | | |
| O-Acetyl-[H$_2$-(2S,3R,4S)Hip$^2$]didemnin A (97) | S | Ist (OAc) | H$_2$Hip | Leu | Pro | Me$_2$Tyr | Thr | D-MeLeu | H | | | | | | |
| [HydroxyiminoHip$^2$]didemnin A (65) | S | Ist | NOHHip | Leu | Pro | Me$_2$Tyr | Thr | D-MeLeu | H | | | | | | |
| Didemnin B Class | | | | | | | | | | | | | | | |
| Didemnin B (17) | N | Ist | Hip | Leu | Pro | Norsta | 2Tyr | Thr | D-MeLeu | Pro | | | | | |
| Nordidemnin B (22) | N | Norsta | Hip | Leu | Pro | Me$_2$Tyr | Thr | D-MeLeu | Pro | D-MeLeu | | | | | |
| Didemnin N (13) | N | Ist | Hip | Leu | Pro | Tyr | Thr | D-MeLeu | Pro | Pro | | | | | |
| Nordidemnin N (14) | N | Norsta | Hip | Leu | Pro | Tyr | Thr | D-MeLeu | Pro | Pro | | | | | |
| [Acetyl$^9$]didemnin B (103) | S | Ist | Hip | Leu | Pro | Me$_2$Tyr | Thr | D-MeLeu | Pro | Pro | | | | | |
| [Propionyl$^9$]didemnin B (104) | S | Ist | Hip | Leu | Pro | Me$_2$Tyr | Thr | D-MeLeu | Pro | Pro | | | | | |
| [Isobutyryl$^9$-L-Pro$^8$]didemnin B (105) | S | Ist | Hip | Leu | Pro | Me$_2$Tyr | Thr | D-MeLeu | Pro | Pro | | | | | |
| [Pyruvyl$^9$]didemnin B (106) | S | Ist | Hip | Leu | Pro | Me$_2$Tyr | Thr | D-MeLeu | Pro | pyruvyl | | | | | |
| [Isobutyryl$^9$-D-Pro$^8$]didemnin B (107) | S | Ist | Hip | Leu | Pro | Me$_2$Tyr | Thr | D-MeLeu | D-Pro | iCOC$_3$H$_7$ | | | | | |
| [L-Ala$^8$]didemnin B (109) | S | Ist | Hip | Leu | Pro | Me$_2$Tyr | Thr | D-MeLeu | Ala | Lac | | | | | |
| [D-Pro$^8$]didemnin B (108) | S | Ist | Hip | Leu | Pro | Me$_2$Tyr | Thr | D-MeLeu | D-Pro | Lac | | | | | |
| [H$_6$—Me$_2$Tyr$^5$]didemnin B (116) | S | Ist | Hip | Leu | Pro | H$_6$Me$_2$Tyr | Thr | D-MeLeu | Pro | Lac | | | | | |
| [H$_6$—MePhe$^5$]didemnin B (118) | S | Ist | Hip | Leu | Pro | H$_6$MePhe | Thr | D-MeLeu | Pro | Lac | | | | | |
| [H$_2$(2S,3S,4S)Hip$^2$]didemnin B (96) | S | Ist | H2Hip | Leu | Pro | Me$_2$Tyr | Thr | D-MeLeu | Pro | Lac | | | | | |
| Phthalimide didemnin B (82) | S | Ist | Hip | Leu | Pro | Me$_2$Tyr | Thr | D-MeLeu | Pro | PhthaLac | | | | | |
| [Anhydroluc$^{11}$]Phthalimide didemnin B (83) | S | anIst | Hip | Leu | Pro | Me$_2$Tyr | Thr | D-MeLeu | Pro | PhthaLac | | | | | |
| Glutaminyl didemnins | | | | | | | | | | | | | | | |
| pGln-didemnin B (113) | S | Ist | Hip | Leu | Pro | Me$_2$Tyr | Thr | D-MeLeu | Pro | Lac | pGlu | | | | |
| Didemnin M (12) | N | Ist | Hip | Leu | Pro | Me$_2$Tyr | Thr | D-MeLeu | Pro | Lac | Gln | pGlu | | | |
| Didemnin E (20) | N | Ist | Hip | Leu | Pro | Me$_2$Tyr | Thr | D-MeLeu | Pro | Lac | Gln | Gln | pGlu | | |
| Didemnin D (19) | N | Ist | Hip | Leu | Pro | Me$_2$Tyr | Thr | D-MeLeu | Pro | Lac | Gln | Gln | Gln | Hydec | |
| Didemnin X (10) | N | Ist | Hip | Leu | Pro | Me$_2$Tyr | Thr | D-MeLeu | Pro | Lac | Gln | Gln | Gln | Hydec | Hydec |
| Didemnin Y (11) | N | Ist | Hip | Leu | Pro | Me$_2$Tyr | Thr | D-MeLeu | Pro | Lac | Gln | Gln | Gln | Hydec | Hydec |
| [Dab$^{10,11,12}$]didemnin X (80) | S | Ist | Hip | Leu | Pro | Me$_2$Tyr | Thr | D-MeLeu | Pro | Lac | DAB | DAB | DAB | Hydec | |
| [Dab$^{10,11,12,13}$]didemnin Y (81) | S | Ist | Hip | Leu | Pro | Me$_2$Tyr | Thr | D-MeLeu | Pro | Lac | DAB | DAB | DAB | DAB | Hydec |

[a] N = natural, isolated from *T. solidum*. S = semisynthetic.
[b] All common amino acids are L unless noted. Subunit abbreviation: see below.
[c] DAB = α,γ-diaminobutyril.

Structure of Unusual Subunits and Their Abbreviation in Table XV

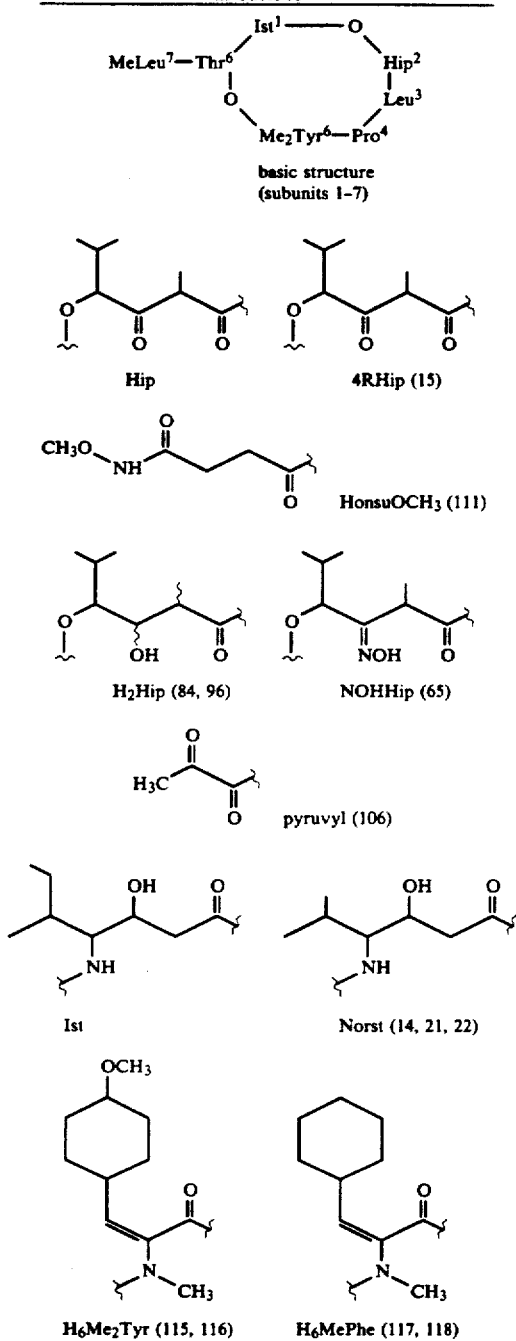

-continued
Structure of Unusual Subunits and Their Abbreviation in Table XV

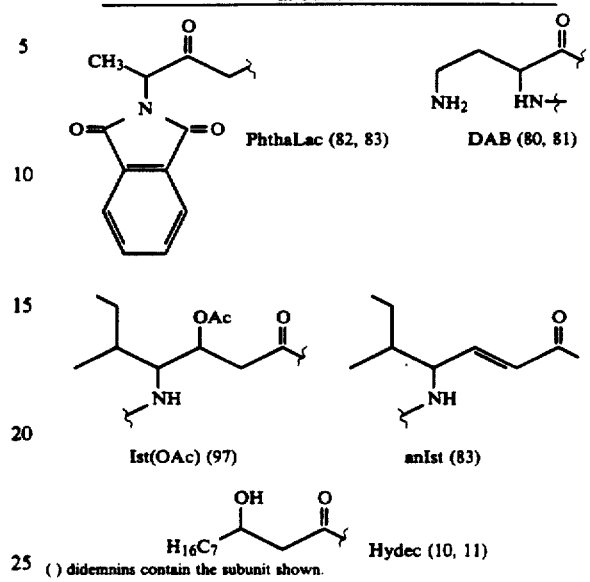

( ) didemnins contain the subunit shown.

BIOLOGICAL ACTIVITIES

All natural and semisynthetic didemnins obtained in this embodiment of the invention were assayed for biological activity. Cytotoxicity and antiviral activities were measured; L1210 cytotoxicities were determined; and immunosuppressive data were obtained. The results are provided in Tables 9-13 below.

L1210 murine leukemia cells were used for the cytotoxicity assay. Didemnin A or B was used as a standard in each assay for accurate comparison. Results are shown in IC$_{50}$ (50% inhibitory concentration) or percent inhibition. For antiviral assays the RNA virus vesicular stomatitis virus (VSV), the DNA virus: Herpes simplex virus Type I (HSV-1), and Visna virus (VIV) were used. Visna virus is a lentivirus which has reverse transcriptase activity, and was proposed as a safer mimic of human immunodeficiency virus (HIV). See, Frank, K. B., et al., Antimicrob. Agents Chemother., 1987, 31, 1369-1374.

The immunosuppressive assay was performed by measuring competitive binding of tested compounds with [$^3$H]didemnin B to Nb2 cells, rat T-cell node lymphoma. See, Russell, D. H., et al., J. Immunology, 1987, 138, 276-284.

Also inhibitions of protein and DNA synthesis of several compounds were measured using Nb2 node lymphoma cells which were stimulated by a treatment of cells with prolactin. (ibid.)

Compound 106 was prepared semisynthetically for in vivo antitumor testing in mice. These results are shown in Table 13.

TABLE 9

Antiviral Activity and Cytotoxicity of Didemnins.[a]

| | | | | Antiviral[b] | | | | | Cytotoxicity |
|---|---|---|---|---|---|---|---|---|---|
| | HSV/VSV[c] | | | | | VIV | | | L1210 |
| | Conc. µg/ml | BHK | VSV | Conc. µg/mL | CV-1 | HSV-1 | Conc. µg/mL | Protection % | Toxicity % | IC$_{50}$ ng/mL |

| Didemnin A-Type | | | | | | | | | | |
|---|---|---|---|---|---|---|---|---|---|---|
| Didemnin A (1) | 1 | 0, PT | + | 10 | 12 | +++ | 1 | ND | 54 | 30 |
| (RS4-75-1) | .5 | 0, PT | + | 5 | 8 | ± | 0.5 | ND | 29 | |

TABLE 9-continued

Antiviral Activity and Cytotoxicity of Didemnins.[a]

| | | | | | | | | | | |
|---|---|---|---|---|---|---|---|---|---|---|
| | .2 | 0 | ± | 2 | 5 | — | 0.2 | ND | 17 | |
| | .1 | 0 | — | 1 | 5 | — | 0.1 | <0 | 5 | |
| Nordidemnin A (21) | 1 | 0, PT | ++ | 10 | 6 | ± | 1 | ND | 17 | 30 |
| (RS4-75-3) | .5 | 0, PT | + | 5 | 5 | ± | 0.5 | ND | 30 | |
| | .2 | 0, PT | + | 2 | 0 | — | 0.2 | ND | 19 | |
| | .1 | 0, | ± | 1 | 0 | — | 0.1 | <0 | 0 | |
| Epididemnin A (15) | 10 | 0, PT | ± | 10 | 0 | — | 1 | <0 | 0 | 300 |
| (RS6-18-1) | 5 | 0 | — | 5 | 0 | — | 0.5 | <0 | −13 | |
| | 2 | 0 | — | 2 | 0 | — | 0.2 | <0 | −4 | |
| Isodidemnin A$_1$ (1a) | 1 | 0, PT | + | 10 | 13, Ls | +++ | 1 | ND | 69 | 10 |
| (RS6-4-4C) | .5 | 0, T | ± | 5 | 10 | + | 0.5 | ND | 43 | |
| | .2 | 0, PT | — | 2 | 8 | ± | 0.2 | ND | 25 | |
| | .1 | 0, PT | — | 1 | 6 | — | 0.1 | <0 | 10 | |
| O-Acetyldidemnin A (114) | 10 | 0, PT | ± | 10 | 11 | — | 1 | <0 | −14 | 300 |
| (RS4-52-1) | 5 | 0, PT | ± | 5 | 8 | — | 0.5 | <0 | −12 | |
| | 2 | 0, PT | — | 2 | 8 | — | 0.2 | < | 1 | |
| | 1 | 0, PT | — | 1 | 5 | — | 0.1 | <0 | −1 | |
| N-Acetyldidemnin A (54) | 1 | 0, PT | +++ | 10 | 10, Ls | +++ | 1 | ND | ND | 0.3 |
| (RS4-51-1) | .5 | 0, PT | ++ | 3 | 10, Ls | +++ | 0.5 | ND | ND | |
| | .2 | 0, PT | ++ | 1 | 8, Ls | +++ | 0.2 | ND | ND | |
| | .1 | 0, PT | ++ | .3 | 0, Ls | ++ | 0.1 | 1 | 94 | |
| | .1 | 0 | ± | | | | | | | |
| Diacetyldidemnin A (32) | 1 | 8, PT | ++ | 10 | 7, Ls | ++ | 1 | ND | ND | 15 |
| (RS4-50-1) | .5 | 0, PT | + | 3 | 7, Ls | + | 0.5 | ND | 96 | |
| | .2 | 0, PT | ± | 1 | 0, Ls | ± | 0.2 | ND | 50 | |
| | .1 | 0, PT | | .3 | 0 | — | 0.1 | <0 | −3 | |
| N-(L-Pro)Didemnin A | 1 | 0, PT | +++ | 10 | 0, Ls | +++ | 1 | ND | ND | |
| (100) | .5 | 0, PT | ++ | 3 | 0, Ls | + | 0.5 | ND | ND | 4 |
| (RS4-76-2) | .2 | 0, PT | + | 1 | 0 | ± | 0.2 | ND | 81 | |
| | .1 | 0, PT | ± | .3 | 0 | — | 0.1 | <0 | 58 | |

| | | Antiviral[b] | | | | | | | | Cytotoxicity |
|---|---|---|---|---|---|---|---|---|---|---|
| | | HSV/VSV[c] | | | | | VIV | | | L1210 |
| | Concentration µg/ml | BHK | VSV | Conc. µg/mL | CV-1 | HSV-1 | Conc. µg/mL | Protection % | Toxicity % | IC$_{50}$ ng/mL |
| N-(D-Pro)Didemnin A | 1 | 0, PT | + | 10 | 0, Ls | ++ | 1 | ND | 48 | 60 |
| (101) | .5 | 0, PT | ± | 3 | 5 | ± | 0.5 | ND | 14 | |
| (RS4-79-2) | .2 | 0, PT | ± | 1 | 0 | ± | 0.2 | ND | 1 | |
| | .1 | 0 | — | .3 | 0 | — | 0.1 | ND | −12 | |
| N-(L-Leu)Didemnin A | 1 | 0, PT | — | 10 | 8, Ls | +++ | 1 | ND | ND | 4 |
| (99) | .5 | 0, PT | — | 3 | 8, Ls | ± | 0.5 | ND | 92 | |
| (RS4-75-2) | .2 | 0, PT | — | 1 | 5 | — | 0.2 | ND | 77 | |
| | .1 | 0, PT | | .3 | 0 | — | 0.1 | ND | 39 | |
| (N-Propionyl)Didemnin | 1 | 0, PT | +++ | 10 | 8, Ls | +++ | 1 | ND | ND | 0.3 |
| A (98) | .5 | 0, PT | ++ | 3 | 8, Ls | +++ | 0.5 | ND | ND | |
| (RS4-80-1) | .2 | 0, PT | + | 1 | 8, Ls | +++ | 0.2 | ND | ND | |
| | .1 | 0, PT | ± | .3 | 6, Ls | + | 0.1 | 1 | 92 | |
| | | | | .1 | 6 | ± | | | | |
| Didemnin B-Type | | | | | | | | | | |
| Didemnin B (17) | 1 | 12, PT | +++ | 10 | 0, Ls | +++ | .1 | ND | ND | 0.5 |
| (RS4-82-1) | .1 | 12, PT | + | 3 | 0, Ls | +++ | 0.03 | ND | ND | |
| | .01 | 0 | ± | 1 | 0, Ls | +++ | 0.01 | −170 | 9 | |
| | .001 | 0 | — | .3 | 0 | ++ | 0.003 | −43 | −24 | |
| | | | | .1 | 0 | ± | | | | |
| | | | | .01 | 0 | — | | | | |
| [Acetyl$^9$]Didemnin B (103) | 1 | 0, PT | ++ | 10 | 0, Ls | +++ | 0.1 | ND | ND | 0.2 |
| (RS4-55-2) | .1 | 0, PT | + | 3 | 0, Ls | +++ | 0.03 | ND | ND | |
| | .01 | 0, PT | — | 1 | 0, Ls | +++ | 0.01 | ND | 49 | |
| | .001 | 0 | | .3 | 0, Ls | ++ | 0.003 | −123 | 3 | |
| | | | | .1 | 0 | ± | | | | |
| | | | | .01 | 0 | — | | | | |
| [Isobutyryl$^9$-L-Pro$^8$] | 1 | 0, PT | +++ | 10 | 0, Ls | +++ | 0.1 | ND | ND | 0.2 |
| Didemnin B (105) | .1 | 0, PT | + | 3 | 0, Ls | +++ | 0.03 | ND | 68 | |
| (RS4-57-1) | .01 | 0, PT | — | 1 | 0, Ls | +++ | 0.01 | ND | 33 | |
| | .001 | 0, PT | — | .3 | 0, Ls | ++ | 0.003 | −93 | 5 | |
| | | | | .1 | 0 | ± | | | | |
| | | | | .01 | 0 | — | | | | |
| [Isobutyryl$^9$-D-Pro$^8$] | 1 | 0, PT | ++ | 10 | 0, Ls | +++ | 0.1 | ND | 19 | 10 |
| Didemnin B (107) | .1 | 0, PT | + | 3 | 0, Ls | ++ | 0.03 | −43 | −21 | |
| (RS4-57-2) | .01 | 0 | — | 1 | 0, Ls | + | 0.01 | −11 | −22 | |
| | | | | .3 | 0 | ± | 0.003 | 0 | −15 | |
| | | | | .1 | 0 | — | | | | |
| [Pyruvyl$^9$]Didemnin | 1 | 0, PT | +++ | 10 | 0, Ls | +++ | 0.1 | ND | ND | 0.2 |
| B (106) | .1 | 0, PT | ± | 3 | 0, Ls | +++ | 0.03 | ND | 74 | |
| (=Dehydrodidemnin B) | .01 | 0, PT | — | 1 | 0, Ls | +++ | 0.01 | ND | 33 | |
| (RS4-82-2) | .001 | 0, PT | — | .3 | 0, Ls | +++ | 0.003 | −92 | −5 | |
| | | | | .1 | 0 | ± | | | | |
| | | | | .01 | 0 | — | | | | |
| (RS4-68-1) | 0.1 | 0, PT | + | 3 | 0, Ls | +++ | 0.03 | ND | 26 | |
| | 0.01 | 0 | — | 1 | 0, Ls | ++ | 0.01 | ND | 3 | |

TABLE 9-continued

Antiviral Activity and Cytotoxicity of Didemnins.[a]

| Compound | Dose | | | | | | Dose | | | |
|---|---|---|---|---|---|---|---|---|---|---|
| | | 0.3 | 0 | + | | | 0.003 | −39 | −22 | |
| | | 0.1 | 0 | − | | | | | | |
| [D-Pro[8]]Didemnin B (108) (RS4-74-1) | 1 | 0, PT | ++ | 10 | 0, Ls | ++ | 0.1 | ND | 20 | 10 |
| | 0.1 | 0, PT | ± | 3 | 0 | + | 0.03 | −83 | −3 | |
| | 0.01 | 0, PT | − | 1 | 0 | − | 0.01 | −24 | −25 | |
| | | | | | | | 0.003 | −11 | −10 | |
| Nordidemnin B (22) (RS4-80-2) | 1 | 0, PT | +++ | 10 | 0, Ls | +++ | 0.1 | ND | 73 | 1 |
| | 0.1 | 0, PT | + | 1 | 0, Ls | +++ | 0.03 | ND | 37 | |
| | 0.01 | 0, PT | ± | 3 | 0, Ls | ++ | 0.01 | ND | 9 | |
| | 0.001 | 0, PT | ± | 0.3 | 0 | + | 0.003 | −25 | −27 | |
| | | | | 0.1 | 0 | − | | | | |
| Didemnin N (13) | 0.1 | 0, PT | − | 3 | 0 | − | 0.03 | 1 | −32 | 30 |
| | 0.01 | 0, PT | − | 1 | 0 | − | 0.01 | 7 | −12 | |
| | 0.001 | 0 | − | | | | 0.003 | 18 | −8 | |
| [Propionyl[9]]Didemnin B (104) (RS4-56-1) | 1 | 0, PT | +++ | 10 | 16 | | 0.1 | ND | ND | 0.2 |
| | 0.1 | 0, PT | + | 3 | 0, Ls | +++ | 0.03 | ND | 74 | |
| | 0.01 | 0, PT | ± | 1 | 0, Ls | +++ | 0.01 | ND | 39 | |
| | 0.001 | 0, PT | ± | 0.3 | 0, Ls | ++ | 0.003 | −113 | 3 | |
| | | | | 0.1 | 0 | ± | | | | |

Others

| Compound | Dose | | | | | | Dose | | | |
|---|---|---|---|---|---|---|---|---|---|---|
| Didemnin E (20) (RS3-46-4) | 1 | T | − | 10 | 0, Ls | +++ | 0.1 | ND | ND | 0.5 |
| | 0.1 | 10, PT | + | 1 | 0, Ls | ++ | 0.03 | ND | 64 | |
| | 0.01 | 0 | − | 0.1 | 0 | − | 0.01 | ND | 28 | |
| | | | | | | | 0.003 | −73 | −4 | |
| Didemnin D (19) (RS3-46-3) | 1 | T | − | 10 | 0, Ls | +++ | 0.1 | ND | ND | 0.5 |
| | 0.1 | 8, PT | + | 1 | 0, Ls | ++ | 0.03 | ND | 66 | |
| | 0.01 | 0 | − | 0. | 0 | − | 0.01 | ND | 27 | |
| | | | | | | | 0.003 | −53 | −10 | |
| Didemnin X (10) (RS3-46-2) | 1 | T | − | 10 | 0, Ls | +++ | 0.1 | ND | ND | 2 |
| | 0.1 | 10, PT | + | 1 | 0, Ls | ++ | 0.03 | ND | 47 | |
| | 0.01 | 0 | − | 0.1 | 0 | − | 0.01 | ND | 6 | |
| | | | | | | | 0.003 | −25 | −21 | |
| Didemnin Y (11) (RS3-46-2) | 1 | 12, PT | + | 10 | 0, Ls | +++ | 0.1 | ND | ND | 2 |
| | 0.1 | 6, PT | | 1 | 0, Ls | ++ | 0.03 | ND | 49 | |
| | 0.01 | 0 | − | 0.1 | 0 | − | 0.01 | ND | 13 | |
| | | | | | | | 0.003 | −33 | −16 | |
| Didemnin M (12) (RS3-47-1) | 1 | T | − | 10 | 0, Ls | +++ | 0.1 | ND | ND | 0.4 |
| | 0.1 | 8, PT | − | 1 | 0 | − | 0.03 | ND | 71 | |
| | 0.01 | 0 | − | 0.1 | 0 | − | 0.01 | ND | 31 | |
| | | | | | | | 0.003 | −73 | 0 | |
| pGlu-didemnin B (113) (RS3-40-1) | 1 | T | − | 10 | 0, Ls | +++ | 0.1 | ND | ND | 0.4 |
| | 0.1 | 8, PT | + | 1 | 0, Ls | +++ | 0.03 | ND | 66 | |
| | 0.01 | 6 | | 0.1 | 0 | − | 0.01 | ND | 30 | |
| | 0.001 | 0 | − | | | | 0.003 | −65 | −5 | |
| [DAB[10,11,12]][3]Didemnin E (RS4-77-1) | 1 | T | − | 10 | 0, Ls | +++ | 0.1 | ND | ND | 1 |
| | 0.1 | 8 Pt | + | 1 | 0, Ls | +++ | 0.03 | ND | 47 | |
| | 0.01 | 6 | | 0.1 | 0 | − | 0.001 | ND | 14 | |
| | 0.001 | 0 | − | | | | 0.003 | −11 | −21 | |
| [HydroxyiminoHip[2]]-Didemnin A (65) (RS4-82-3) | 1 | T | − | 10 | 0 | + | 0.1 | ND | 9 | 20 |
| | 0.1 | 10 Pt | − | 1 | 0 | ± | 0.03 | ND | −3 | |
| | 0.01 | 0 | − | 0.1 | 0 | − | 0.01 | −33 | −14 | |
| | 0.001 | | | | | | 0.003 | −14 | −12 | |
| O-Acetyl-[H[2]-(2S,3R,4S)Hip[2]]-Didemnin A (97) (RS4-52-2) | 5 | 10 | 0 | ± | | | 0.1 | −13 | −4 | 1000 |
| | 0.1 | 0 | − | 1 | 0 | − | 0.03 | −13 | −1 | |
| | 0.01 | 0 | − | 0.1 | 0 | − | 0.01 | ND | ND | |
| | | | | | | | 0.003 | −5 | −2 | |
| Acyclodidemnin A (16) (RS6-17-1) | 1 | 5 | − | 10 | 0 | ± | 0.1 | ND | −3 | 30 |
| | 0.1 | 0 | − | 1 | 0 | − | 0.03 | −20 | −27 | |
| | 0.01 | 0 | − | 0.1 | 0 | − | 0.01 | 0 | −6 | |
| | | | | | | | 0.003 | 4 | −3 | |
| N-(CH[3]ONsu)-didemnin A (111) (RS4-73-1) | 1 | T | − | 10 | 0, Ls | +++ | 0.1 | ND | 67 | 1 |
| | 0.1 | 12 Pt | − | 1 | 0, Ls | ++ | 0.03 | ND | 25 | |
| | 0.01 | 0 | − | 0.1 | 0 | − | 0.01 | ND | 0 | |
| | 0.001 | 0 | − | | | | 0.003 | −43 | −26 | |

[a] Assays performed by Dr. R. G. Hughes, Roswell Park Memorial Institute, N. Y.
[b] Abbreviations: BHK = Baby hamster kidney cells, VSV = vesicular stomatitis virus, HSV = Herpes simlex virus Type-1, CV-1 = CV-1 monkey kidney cells, VIV = Visna virus. PT = Partial toxicity. ND = Not determined, T = Toxic, Ls = Light staining (toxic).
[c] Activities are listed as: +++ = very strong, ++ = strong, + = moderate, ± = marginal, − = inactive.

TABLE 10

L1210 Cytotoxicity of Didemnins[a]

| Compounds | Date tested | Dose (ng/mL) | | | |
|---|---|---|---|---|---|
| | | 250 | 25 | 2.5 | 0.25 |
| | | Inhibition (%) | | | |
| [H[6]Me[2]Tyr[5]]didemnin A (115) | 4/22/1990 | 94 | 17 | 0 | |
| [H[6]-N-MePhe[5]]didemnin A (117) | 4/22/1990 | 98 | 75 | 33 | NT |
| [H[6]Me[2]Tyr[5]]didemnin B (116) | 4/22/1990 | 99 | 98 | 87 | NT |
| [H[6]-N-MePhe[5]]didemnin B (118) | 4/22/1990 | 99 | 99 | 83 | NT |

TABLE 10-continued

L1210 Cytotoxicity of Didemnins[a]

| Compounds | Date tested | Dose (ng/mL) Inhibition (%) | | | |
|---|---|---|---|---|---|
| | | 250 | 25 | 2.5 | 0.25 |
| Didemnin A (1) | 4/22/1990 | 100 | 80 | NT | |
| Acyclodidemnin A (16) | 4/18/1991 | 99 | 25 | 0 | |
| Acyclodidemninn A (hydrolyzed, 66) | 4/18/1991 | 99 | 56 | 0 | |
| [H$_6$-N-MePhe$^5$]didemnin A (117) | 4/18/1991 | 94 | 25 | 0 | |
| [H$_6$Me$_2$Tyr$^5$]didemnin B (116) | 4/18/1991 | 99 | 99 | 75 | 0 |
| [H$_6$-N-MePhe$^5$]didemnin B (118) | 4/18/1991 | 99 | 99 | 90 | 13 |
| Didemnin B (17) | 4/18/1991 | 99 | 99 | 87 | 6 |
| Phthalimidedidemnin B (82) | 4/18/1991 | 99 | 98 | 6 | 0 |
| [AnhydroIst$^1$]phthalimidedidemnin B (83) | 4/18/1991 | 99 | 81 | 0 | |

[a]Performed by Dr. G. R. Wilson in this laboratory.

TABLE 11

Inhibitory Effects of Didemnin Analogs on the Binding of [$^3$H]Didemnin B to Nb2 Cells.[a]

| Compound | Concentration μg/mL Inhibition[b] (%) | | | | IC$_{50}$ ng/mL | Ratio[c] |
|---|---|---|---|---|---|---|
| | 1 | 0.1 | 0.01 | 0.001 | | |
| Didemnin B (17) | 77 | 59 | 7 | 3 | 88 | 293 |
| [Acetyl$^9$]didemnin B (103) | 85 | 67 | 2 | 3 | 63 | 315 |
| [Isobutyryl$^9$-L-Pro$^8$]-didemnin B (105) | 75 | 59 | 4 | 2 | 97 | 485 |
| [Isobutyryl$^9$-D-Pro$^8$]-didemnin B (107) | 69 | 25 | 0 | 0 | 179 | 18 |
| [D-Pro]didemnin B (109) | 74 | 41 | 0 | 0 | 168 | 2.8 |
| Didemnin N (13) | 10 | 4 | 6 | 3 | 1 g | |
| Didemnin A (1) | 35 | 20 | 8 | 3 | 30000 | 1000 |
| N-Acetyldidemnin A (54) | 80 | 72 | 12 | 2 | 57 | 190 |
| N-Propionyldidemnin A (98) | 72 | 40 | 2 | 3 | 179 | 596 |
| O-Acetyldidemnin A (114) | 10 | 15 | 4 | 1 | >1 mg | |
| Epididemnin A (15) | 12 | 9 | 3 | 0 | >1 g | |
| O-Acetyl-[H$_2$-(2S,3R,4S)Hip$^2$]-didemnin A (97) | 19 | 2 | 0 | 0 | >1 mg | |
| Acyclodidemnin A (16) | 8 | 6 | 7 | 0 | 1 g | |

[a]Competing didemnins incubated with approximately 25 ng of [$^3$H]didemnin B per sample for 3 h at 37° C.
[b]Percentages averaged from multiple experiments.
[c]Ratio of IC$_{50}$ of [[$^3$H]didemnin B binding/L1210 growth].

TABLE 12

Inhibition of Ongoing DNA and Protein Synthesis.

| Compound | IC$_{50}$[b] DNA ng/mL | Protein ng/mL | Ratio[c] |
|---|---|---|---|
| N-acetyldidemnin A (54) | 70 | 13 | 0.73 |
| Didemnin B (170) | 90 | 44 | 0.31 |
| Didemnin A (1) | 2000 | 70 | 1.45 |
| Didemnin N (13) | 200,000 | 1,000,000,000 | −0.70 |
| O-Acetyldidemnin A (114) | 270,000 | 1,000,000,000 | −0.57 |
| Acyclodidemnin A (16) | inactive (1 g) | inactive (1 g) | |
| Epididemnin A (15) | inactive (1 g) | 1 mg | 3 |

[a]Nb2 cells were stimulated with prolactin for 24 h, then exposed to didemnins in the presence of radiolabled precursors. (see Ref. 103)
[b]50% Inhibitory concentration, calculated with linear regression analysis.
[c]Log IC$_{50}$ of (DNA/Protein) synthesis.

TABLE 13

In Vivo Activities of Dehydrodidemnin B ([Pyruvyl$^9$]didemnin B, 106) in Mice[a]

| Dose[b] μg/kg/day | Body wt. chenge. (g) | Day of death | Median Survival (day) | T/C[c] (%) | Alive (day 23) |
|---|---|---|---|---|---|
| P388[d] | | | | | |
| 320 | −3.3 | 4, 5, 6, 6, 9 | 6.0 | 60 | 0 |
| 160 | −3.2 | 10, 19, 21, 21, 22, 22 | 21.0 | 210 | 0 |
| 80 | −1.4 | 13, 19, 19, 20, 20, 20 | 19.5 | 195 | 0 |
| B16[e] | | | | | (day 24) |
| 160 | −1.3 | 15, 31, 32, 32, 36, 38, 38, 39, 41, 42 | 37 | 218 | 0 |
| 80 | −0.5 | 30, 31, 31, 32, 32, 32, 32, 33, 34, 35 | 32 | 188 | 0 |
| 40 | 0.1 | 29, 29, 29, 30, 30, 30, 31, 31, 32, 32 | 30 | 178 | 0 |

| Dose μg/kg/day | Body Wt. Chenge. (g) | Lewis Lung[f] N. P.[g] (Day 14) | Median Tumor Vol. (mm$^3$) | T/C[h] (%) |
|---|---|---|---|---|
| 160 | −3.7 | 5 | 0 | 0.00 |
| 80 | −4.5 | 2 | 163 | 0.13 |
| 40 | −2.6 | 0 | 473 | 0.37 |

[a]Assays were carried out by Athur D. Little Inc.
[b]Schedule 1-9 days i. p.
[c]Treated/control, Significant activity: >125%.
[d]P388 murine lymphoma. Median survival of control mice, 10.0 days.
[e]B16 melanoma. Median survival of control mice, 17.0 days.
[f]Lewis lung carcinoma, median tumor volume of control mice 1372 mm$^3$.
[g]N. P. = number of non-palpable tumors on day 14.
[h]Significant activity: T/C <0.40.

Isolation of Didemnin M (Compound 12)

A portion of the Fraction A CH$_2$Cl$_2$ extract obtained from The Upjohn Company (21 g) was partitioned between the upper and lower layers of ethyl acetate-heptane-methanol-water (7:4:4:3) to give a green gum (12 g) from the lower layer (Fraction B$^J$). Fraction B$^J$ was separated by silica gel chromatography (Alfa gel 0.6 kg) with chloroform-methanol (8:1) into 12 fractions (Fraction B$^J$-1 to -12). A portion (270 mg) of Fraction B$^J$-5 was further separated by a silica gel column (Kieselgel 60, 60 g) with chloroform-methanol (8:1) into nine fractions (Fraction 2-1 to -9). Fraction 2-6 (26 mg) was passed through a short silica gel column (Kieselgel 60, 1 g, treated with ammonia gas prior to use) with chloroform-methanol (4:1). The resulting solid, upon evaporation of solvent, was purified by HPLC on a reversed-phase C-18 column with methanol-water (10:1, retention time 8.4 min.,) to give didemnin M (12, 10 mg, white powder): m.p. 158°-160° C.; [alpha]$_D$25°−68.4° (c, 1.1, CHCl$_3$) IR (film) 3340, 2960, 1734, 1637 cm$^{-1}$; UV (CH (CH$_3$OH) $\lambda_{max}$ 204 (log ε 4.76), 224 (4.38); $^1$H NMR (CDCl$_3$, 300 MHz) 7.95 (1H, d, J=8.7) 7.40 (1H, J=9.3), 7.28 (1H, br s), 7.07 (2H, d, J=8.4), 6.84 (2H, d, J=8.4), 6.62 (1H, br s), 5.81 (1H, br s), 3.79 *3H, s), 3.40 (3H, s), 2.54 (3H, s), 1.48 (3H, d, J=6.9), 1.40 (3H, d, J=6.3), 1.33 (3H, d, J=6.6); $^{13}$C NMR (CDCl$_3$, 75 MHz) 204.7, 178.6, 176.3, 173.1, 172.4, 172.1, 172.0, 171.2, 170.4, 171.1, 169.6, 169.5, 168.3, 158.6, 130.3, 129.8, 114.1, 81.4, 71.0, 70.9, 70.5, 69.3, 67.5, 66.2, 59.0, 57.2, 56.8, 56.6, 56.5, 55.9, 55.3, 54.3, 53.4, 51.8, 49.7, 49.6, 47.0, 41.3, 38.6, 37.3, 36.2, 34.1, 33.9, 31.2, 31.0, 29.3, 28.8, 27.9, 26.9, 25.7, 25.6, 25.5, 25.3, 25.0, 24.8, 24.5, 23.8, 23.6, 21.3, 20.9, 18.7, 16.7, 15.9, 15.2, 14.8, 11.6; FABMS m/Z 1352 (M+H), 536, 381, 312, 240; Anal. Calcd. for C$_{67}$H$_{103}$N$_{10}$O$_{19}$ (M+H) 1351.1800. Found: 1351.1791, (M+H) (HRFABMS).

Isolation of Isodidemnin A$_1$ (Compound 1a), Didemnin N (Compound 13), Nordidemnin N (Compound 14), Epididemnin A (Compound 15) and Acyclodidemnin A (Compound 16)

A second batch of Fraction A (97 g) was partitioned as above to give Fraction B$^{II}$ (50 g), which was chromatographed on a silica gel column (Alfa gel 1.2 kg) with chloroform-methanol (8:1) into 13 fractions B$^{II}$-1 to 13, Table 7b). Fraction B$^{II}$-4 (1.05 g) was further separated by CCC with ethyl acetate-cyclohexane-toluene-methanol-water (7:2:2:4:4), using the upper layer as mobile phase with a flow rate of 2 ml/min., into 19 original fractions (12 ml/fraction) which were combined by TLC (silica gel, chloroform-methanol, 4 to 8:1) into five fractions (Fraction B$^{II}$-4-1 to -5). Fraction B$^{II}$-4-2 (378 mg) was then separated on a Sephadex LH-20 column with methanol into Fractions C-G Fraction D (94.7 mg) was further separated by a silica gel column with chloroform-methanol (10:1) into six fractions. Fraction 4, readily crystallized from acetone, was recrystallized from the same solvent to give 4.4 mg of isodidemnin A$_1$ (Compound 1a).

Isodidemnin A$_1$ (Compound 1a), colorless prisms, showed the following physical properties: m.p. 162°-166° C.; [α]$_D$24−143° (c, 0.44, CHCl$_3$); IR (film) 3348, 2959, 1732, 1635, 1512, 1074 cm$^{-1}$; FABMS m/z 943; Anal. Calcd. for C$_{49}$H$_{79}$N$_6$O$_{12}$: M$_n$ 943.5756 (M+H). Found: M$_n$ 943.5773 (M+H) (HRFABMS).

Fraction E was further separated by a silica gel column (Bio Rad TLC grade gel) with ethyl acetate-2-propanol (10:1) followed by HPLC using a silica gel column with ethyl acetate-2-propanol (25:1) to give didemnin N (Compound 13, 17.8 mg) as a first peak [HPLC: C-18, MeOH-H$_2$O (7:2), retention time 22 min.). The second peak was purified by reversed-phase C-18 HPLC with methanol-water (7:2) to give nor-didemnin N (Compound 14, 3.2 mg, retention time 18.8 min.) as the first fraction, and 0.7 mg of didemnin N (Compound 13) as the second fraction.

Didemnin N (Compound 13), a yellowish solid, showed the following physical properties: m.p. 150°-152° C.; [α]$_D$24−49° (c, 1.6, CHCl$_3$); IR (film) 3333, 2959, 1734, 1635 cm$^{-1}$; UV (CH$_3$OH) $\lambda_{max}$ 210 (log 4.43) nm; $^{13}$C NMR 205.0, 173.6, 173.0, 172.5, 172.4, 171.7, 170.5, 170.0, 169.6, 169.1, 155.5, 130.5, 127.9, 115.5, 81.8, 71.5, 67.3, 65.9, 60.6, 57.4, 55.3, 54.9, 54.5, 49.0, 47.2, 47.1, 41.4, 38.7, 36.2, 34.9, 33.4, 31.2, 31.1, 29.0, 28.3, 27.4, 25.9, 25.0, 24.8, 24.7, 23.4, 21.3, 20.8, 20.1, 20.0, 18.8, 16.7, 15.7, 15.2, 13.6, 11.8; FABMS m/Z 1085, 297; Anal. Calcd. for C$_{55}$H$_{86}$N$_{15}$O$_7$: M$_n$ 1084.6182 (M+H). Found; M$_n$ 1084.6187 (M+H) (HRFABMS).

Nordidemnin N (Compound 14), a white power, showed the following physical properties: m.p. 154°-156° C.; [α]$_D$24−54° (c, 0.13, CHCl$_3$); IR (film) 3323, 2929, 1734, 1635, 752 cm$^{-1}$; Uv (CH$_3$OH) $\lambda_{max}$ 210 (log 4.43) nm; $^1$H NMR (500 MHz, CDCl$_3$) 7.87 (1H, d, J=9.0), 7.58 (1H, d, J=7.0), 7.16 (1H, br d, J=10.0), 6.99, (2H, J=8.5), 6.74 (1H, d, J=8.5), 5.95 (1H, d, J=8.0), 5.40 (1H, dd, J=3.0, 11.5, MeLeu ), 5.20 (1H, d, J=3.0, Hip-H-4), 5.02 (1H, m), 4.77 (3H, m), 4.68 (1H, br d, J=5.0), 4.44 (1H, q, J=7.5), 4.40 (1H, q, J=7.0), 4.24 (2H, m), 4.02 (1H, t, J=9.5), 3.92 (1H, dt, J=3.5, 9.5), 3.70 (2H, m), 3.6 (1H, m), 3.47 (1H, m), 3.14 (3H, s), 1.40 (3H, d, J=7.0), 1.39 (3H, d, J=7.0), 1.30 (3H, d, 7.0); FABMS m/z 1070 (M+H), 2978; Anal. Calcd. for C$_{54}$H$_{84}$N$_7$O$_{15}$: M$_n$ 1070.5935 (M+H): Found: M$_n$ 1070.5996 (M+H) (HRFABMS).

Epididemnin A (Compound 15)

Fraction B$^{II}$-12 (650 mg, Table 7) was further separated by a silica gel column (70–230 mesh, 85 g) with chloroform-methanol (4:1 1:1, gradient) into 8 fractions (Scheme 4). Fraction (145.5 mg) was separated on a silica gel column with ethyl acetate-2-propanol (15:1). Fraction 5 (9.2 mg) was purified on a silica gel (2–10 μm) column with chloroform-methanol (8:1) to give epididemnin A (Compound 15) as a white power (4.8 mg): m.p. 130°-132° C.; [α]$_D$23−100° (c, 0.13, CHCl$_3$); IR (film) 3330, 2960, 2874, 1738, 1659, 1649, 1514, 1456, 1169 cm$^{-1}$; UV (CH$_3$OH) $\lambda_{max}$ 206 (log 4.69) 229 (4.49) nm; Anal. Calcd. for C$_{49}$H$_{79}$N$_6$O$_{12}$: M$_n$ 943.5756 (M+H). Found: M$_n$ 943.5776 (M+H) (HRFABMS).

Acyclodidemnin A (Compound 16)

Fraction B$^{II}$-12-2 (Scheme 4) was purified by HPLC (C-18) with methanol-water (8:1) to give 16 (5.8 mg), a white powder: m.p. 126°-130° C.: [α]$_D$26−71° (c, 0.06, CHCl$_3$); IR (film) 3300, 2960, 1732, 1635, 1514, 1456, 1263 cm$^{-1}$; UV (CH$_3$OH) $\lambda_{max}$ 206 (log 4.80), 230 (4.51) nm; FABMS m/z 961 (M+H); FABMS/MS m/z 961, 943, 834, 770, 752, 655, 627, 541, 528, 368, 307, 210, 100, 70; Anal. Calcd. for C$_{49}$H$_{81}$N$_6$O$_{13}$: M$_n$ 961.5862 (M+H). Found: M$_n$ 961.5871 (M+H) (HRFABMS).

Acyclodidemnin A Triacetate (Compound 16a)

Compound 16 (0.86 mg) was treated with acetic anhydride (0.1 ml) in pyridine (0.1 ml) at room temperature for 12 hr., and evaporated. The resulting product, Compound 16a was subjected to analysis by FABMS (m/z 1088); and FABMS/MS (m/z 1088 1070, 919, 782, 321, 307, 210, 170, 142, 100, 70); Anal. Calcd. for C$_{55}$H$_{87}$N$_6$O$_{16}$: M$_n$ 1087.6179 (M+H). Found: M$_n$ 1087.6201 (M+H) (HRFABMS).

Mitsunobu Reaction of Didemnin B (Compound 17)

To a mixture of didemnin B (20 mg, 0.018 mmol), triphenylphosphine (23.6 mg, 0.090 mmol), phthalimide (13.2 mg, 0.090 mmol) and dried tetrahydrofuran (0.5 ml) were added a solution of diethyl azodicarboxylate (16 mg, 0.092 mmol) in tetrahydrofuran (0.5 ml) over 15 min. The reaction was monitored by TLC for 24 hr. at room temperature. The reaction mixture was concentrated by $N_2$, and the resulting solid was separated by a silica (100 μl) of sodium borohydride (1 mg/ml). The mixture was stirred at room temperature for 12 hr. Hydrochloric acid (1N, 9 μl) was added and organic solvent was removed by $N_2$. The product was extracted with dichloromethane to give a solid, which was separated by HPLC (C-18) with methanol-water (7:1) to give Compound 96 (260 μg, 47% conversion) and unreacted didemnin B (450 μg). Anal. Calcd. for $C_{57}H_{92}N_7O_{15}$: $M_n$ 111.4.6651 (M+H). Found: $M_n$ 1114.6657 (M+H) (HRFABMS).

Dihydrodidemnin N (Compound 94)

Didemnin N (Compound 13, 960 μg) was reduced to give (Compound 94) (200 μg) and unreacted 13 (330 μg). Anal. Calcd. for $C_{55}H_{88}N_7O_{15}$: $M_n$ 6339 (M+H). Found: $M_n$ 1086.6369 (M+H) (HRFABMS).

Dihydroepididemnin A (Compound 95)

To a solution of epididemnin A (Compound 15) (930 μg) in tetrahydrofuran (0.5 ml) was added an aqueous solution (100 μl) of sodium borohydride (1 mg/ml). The mixture was stirred at room temperature for 1.5 hr. Hydrochloric acid (1N, 10 μl) was added to the reaction mixture, and the organic solvent was removed by $N_2$ leaving an aqueous suspension. The residue was extracted with dichloromethane to give a mixture of Compound 95 and hydrated Compound 95 upon removal of solvent: FABMS m/z 963 (M+H), 945 (M+H). The mixture was carried to the next step without further purification.

Hydrolysis and Derivation of Dihydrodidemnins—Compounds 84 and 94–97

Each sample of a dihydrodidemnin was hydrolyzed separately with hydrochloric acid (6N) at 80° C. for 12 hr. Each hydrolyzate was pre-column derivatized by a general procedure, and analyzed by GC.

N-Acetyl didemnin A (Compound 54)

To a solution of Compound 1 (10.5 mg, 0.011 mmol) in benzene (0.5 ml) were added acetyl chloride (0.033 mmol) and triethylamine (10 μl). The mixture was allowed to stand at room temperature for 12 hr., and concentrated, and the resulting solid was separated by a short (2 cm) silica gel column (Kieselgel 60) with ethyl acetate to give Compound 54 (10.6 mg, 100%, for HPLC) to a white powder: m.p. 143°–147° C. (lit 124°–126° C.[2a]); $[\alpha]_D^{24}-80°$ (c, 1.1, CHCl₃); IR (film) 3345, 2959, 1734, 1635, 1539, 1456, 1246 cm⁻¹; ¹H NMR (CDCl₃, 500 MHz) 7.95 (1H, d, J=9.0), 7.30 (1H, d, J=10.0), 7.09 (2H, d, J=8.5), 7.04 (1H, d, J=9.0), 6.85 (2H, d, J=8.5), 3.80 (3H, s), 2.88 (3H, s), 2.55 (3H, s), 2.20 (3H, s), 2.00 (3H, s);. FABMS m/z 986 (M+H), 816. Anal. Calcd. for $C_{51}H_{81}N_6O_{13}$: $M_n$ 985.5862 (M+H): Found: $M_n$ 985,5880 (M+H) (HRFABMS).

N,O-Diacetyldidemnin A (Compound 32)

To a solution of Compound 1 (10.0 mg, 0.011 mmol) in pyridine (0.1 ml) was added acetic anhydride (0.1 ml). The mixture was allowed to stand at room temperature for 24 hr., and concentrated, and the resulting solid was separated on a silica gel (Bio Rad TLC grade) column with ethyl acetate to give pure Compound 32 (11.2 mg, 100%) as a white powder: m.p. 130°–133° C. (lit 128°–131° C.[2a]); $[\alpha]_D^{24}-80°$ (c, 1.0, CHCl₃); IR (film) 3327, 2963, 1734, 1695, 1662, 1653, 1635, 1539, 1456, 1221, 1169 cm⁻¹; ¹H NMR (CDCl₃, 500 MHz) 7.98 (1H, d, J=9.0), 7.11 (1H, d, J=12), 7.09 (2H, d, J=8.0), 6.96 (1H, d, J=8.5), 6.86 (2H, d, J=8.5), 3.80 (3H, s), 2.91 (3H, s), 2.55 (3H, s), 2.21 (3H, H s), 2.18 (3H, s); FABMS m/z 1027 (M+H), 858. Anal. Calcd. for $C_{53}H_{83}N_6O_{14}$: 1027.5967 (M+H). Found: 1027.5961 (M+H) (HRFABMS).

N-(D-Prolyl) didemnin A (Compound 101).

a. N-(benzyloxycarbonyl-D-prolyl) didemnin A (Compound 119)

To a solution of N-benzyloxycarbonyl-D-proline (Z-D-Proline, Z-D-Pro, 59 mg, 0.24 mmol) in dichloromethane (0.5 ml) was added dicyclohexyl-carbodiimide (24.4 mg, 0.12 mmol) at 5° C. The mixture was stirred at 5° C. for 2 hr. Compound 1 (75.4 mg, 0.08 mmol) in dichloromethane (0.5 ml) was added to the mixture, which was allowed to stand for 8 hr. at 10° C., then was concentrated in vacuo. The mixture was added to cold ethyl acetate, filtered, and concentrated in vacuo to give an oil which was separated on a silica gel column with ethyl acetate-dichloromethane (7:3) to give Compound 119 (83.9 mg, 0.071 mmol, 89%): m.p. 130°–134° C.; $[\alpha]_D^{26}-52.5°$ (c, 0.28, CHCl₃); IR (film) 3340, 2960, 1732, 1640, 1448, 1514, 1271, 1080 cm⁻¹; ¹H (CDCl₃, 300 MHz) 7.9* (1H, m), 7.2–7.4 (5H, m), 7.05 (2H, d, J=8.4), 6.82 (2H, d, J=8.4), 3.76 (3H, s), 2.88*, 2.89*, 2.77* (s), 2.55*, 2.52* (s). (*peaks were observed as sets.) Anal. Calcd. for $C_{62}H_{92}N_7O_{15}$: $M_n$ 1174.6651 (M+H). Found: $M_n$ 1174.6663, HRFABMS.

b. N-(D-Prolyl) didemnin A (Compound 101)

A mixture of Compound 119 (80 mg, 0.077 mmol) and palladium (10%) on activated carbon (36 mg) in methanol (2 ml) was stirred vigorously in a hydrogen atmosphere for 2 hr. at room temperature, filtered through a C-18 Sep-pak column with methanol, and concentrated to give a white powder (65.5 mg). A portion (17.0 mg) of the solid was separated by HPLC (C-18) with methanol-aqueous sodium chloride (0.4) M) (7:1) to give pure Compound 101 (11.9 mg, 75.4%) from Fraction 1 165°–170°; $[\alpha]_D^{26}-70°$ (c, 0.65, CHCl₃); ¹H NMR (CDCl₃, 300 MHz) 7.97–7.3 (br NH's) 7.07 (2H, d, J=8.4), 6.83 (2H, d, J=8.4), 3.79 (3H, s), 2.92 (3H, br s), 2.53 (3H, s); Anal. Calcd. for $C_{54}H_{86}N_7O_{13}$: 1140.6284 (M+H). Found 1140.6285 (HRFABMS).

N-(L-Prolyl) didemnin A (Compound 100)

Z-L-Pro was coupled to Compound 1 and deprotected as above to give a white powder (27% overall): m.p. 166°–170° C.; ¹H NMR (CDCl₃, 300 MHz) 8.03 (1H, d, J=8.7), 7.73 (1H, br d, J=9.6), 7.33 (1H, br s), 7.06 (2H, d, J=8.4), 6.84 (2H, d, J=8.4, 3.88 (3H, s), 3.02 (3H, s), 2.53 (3H, s); Anal. Calcd. for $C_{54}H_{86}N_7O_{13}$ (M+H): $M_n$ 1040.6284. Found: $M_n$ 1040.6277 (M+H) (HRFABMS).

[Acetyl⁹]didemnin B (Compound 103)

To a suspension of L-Pro (247 mg, 2.15 mmol) in pyridine (1 ml) was added acetic anhydride (1 ml), and the mixture was stirred at room temperature for 5 min. The solvent was removed in vacuo and the resulting oil was partitioned between ethyl acetate and 1N hydrochloric acid. The organic layer was dried over sodium sulfate, and concentrated, and the resulting solid was recrystallized from ethyl acetate to give N-acetyl-L-proline (167 mg, 44%), a white powder: m.p. 108° C. [lit 115° C. (from CHCl₃)⁹⁹]; [α]$_D^{25}$ −171° (c, 0.91, CHCl₃) [(lit[107] −118° (c, 1, H₂O)] Anal. Calcd. for C₇H₁₁NO₃: C, 53.49; H, 7.05, N, 8.91. Found: C, 53.57; H, 7.09; N, 8.76.

N-Acetyl-L-proline (31 mg, 0.197 mmol) was treated with dicyclohexyl carbodiimide (20.3 mg, 0.099 mmol) in dichloromethane (0.1 ml) for 4 hr. at 10° C. To the mixture was added a solution of Compound 1 (62 mg, 0.068 mmol) in CH₂Cl₂—DMF (6:4, 1 ml) at 5° C. The mixture was allowed to stand at 5° C. for 12 hr., then was filtered, and concentrated in vacuo. The resulting solid was separated on a silica gel column with ethyl acetate-2-propanol (10:1) to give Compound 103 (63 mg, 88%); as a white powder: m.p. 152° C.; [α]$_D^{24}$ −85° (c, 1.6, CHCl₃); IR (film) 3327, 2959, 1732, 1637, 1539, 1514, 1450 cm⁻¹; ¹H NMR (CDCl₃, 500 MHz) 7.93 (2H, m), 7.16 (1H, d, J=10.0), 7.07 (2H, d, J=8.5), 6.84 (2H, d, J=8.5), 5.35 (1H, dd, J=3.5, 11.5, MeLeu H-), 5.32 (1H, dq, J=2.0, 6.0, Thr H-), 5.17 (d, J=3.5, Hip-H-4), 4.79 (1H, br t, J=11.0, Leu H-), 4.63 (1H, t, J=7.0), 4.60 (1H, dd, J=8.0, 5.0), 4.52 (1H, m, Thr Ha), 4.23 (1H, q, J=6.5, Hip H-2), 4.15-4.0 (2H, m, 1st H-), 3.79 (3H, s, Me₂Tyr-OCH₃), 3.12 (3H, s, MeLeu-NCH₃), 2.55 (3H, s. Me₂Tyr-NCH₃), 2.09 (3H, s, acetyl), 1.39 (3H, d, J=6.5), 1.32 (1H, d, J=6.0); FABMS m/z 1083 (M+H), 268; Anal. Calcd. for C₅₆H₈₈N₇O₁₄: M$_n$ 1082.6389. Found: M$_n$ 1082.6396 (M+H) (HRFABMS).

[Propionyl⁹]didemnin B (Compound 104)

To a suspension of L-proline (1.15 g, 0.01 mol) in pyridine (2 ml) was added propionic anhydride (2.60 g, 0.02 mol). The mixture was stirred for 30 min. at room temperature. The solvent was removed in vacuo, and the product was recrystallized from ethyl acetate to give N-propionyl-L-proline (1.60 g, 96%): colorless needles; m.p. 98°-99° C.; [α]$_D^{25}$ −186° (c, 1.7, CHCl₃); ¹H NMR (360 MHz) 4.60 (1H, m), 3.57 (1H, m), 3.44 (1H, m), 2.38 (2H, q, J=7.2), 2.00 (4H, m), 1.17 (3H, t, J=7.2). Anal. Calcd. for C₈H₁₃NO₃: C, 56.13; H, 7.65; N, 8.18. Found: C, 56.15; H, 7.67; N, 8.17.

N-Propionyl-L-proline was coupled with Compound 1 (26.4 mg, 0.028 mmol) as in the synthesis of Compound 103 to give [propionyl⁹]didemnin B (104) (28.7 mg, 93%); as a white powder: m.p. 148° C.; [α]$_D^{25}$ −77° (c, 2.9, CHCl₃); IR (film) 3330, 2876, 1730, 1630 cm⁻¹; ¹H NMR (CDCl₃, 500 MHz) 7.98 (1H, d, J=6.0), 7.91 (1H, d, J=9.0), 7.19 (1H, d, J=10.0), 7.06 (2H, d, J=8.4), 6.83 (2H, d, J=8.4), 5.38 (1H, dd, 4.0, 11.5, MeLeu H-), 5.30 (1H, dq, J=2.5, 6.1, Thr H-), 5.16 (d, J=3.5, Hip H-4), 4.79 (1H, br t, J=11.0, Leu H-), 4.63 (1H, t, 7.0), 4.60 (1H, dd, J=8.0, 5.5), 4.52 (1H, dd, J=2.5, 5.5, Thr H-), 4.23 (1H, q, J=6.5, Hip H-2), 4.15-4.0 (2H, m, 1st H-), 3.78 (3H, s, Me₂Tyr-OCH₃), 3.13 (3H, s, MeLeu NCH₃), 2.53 (3H, s, Me₂Tyr NCH₃), 1.41 (3H, d, J=6.0), 1.32 (1H, d, J=7.0), (1.18, 3H, t, J=7.5}; FABMS m/z 1097 (M+H), 281; Anal. Calcd. for C₅₇H₉₀N₇O₁₄: M$_n$ 1096.6556 (M+H). Found: M$_n$ 1096.6572 (M+H) (HRFABMS).

[Isobutyryl⁹]didemnin B (Compound 105) and [Isobutyryl⁹-D-Pro⁸]didemnin B (Compound 107)

L-Proline (1.15 g, 0.01 mol) was treated with isobutyric anhydride in a procedure similar to the N-propionylproline synthesis to give N-isobutyrylproline (1.8 g, 96%): fine crystals; m.p. 80°-82° C.; [α]$_D^{25}$ −8.7° (c, 1.56, CHCl₃); ¹H NMR 4.55 (1H, m), 3.60 (2H, m), m), 2.70 (1H, sept, J=7.2), 1.8-2.0 (4H, m), 1.14 (3H, d, J=7 2), 1.12 (3H, d, J=7.2). Anal. Calcd. for Calcd. for C₉H₁₅NO₃: C, 58.36, H, 8.16; N, 7.64. Found: C, 58.26; H, 8.10; N, 7.64.

N-Isobutyrylproline was coupled with Compound 1 (26.4 mg, 0.028 mmol) using the method described above for the preparation of Compound 103. The product was separated on a silica gel column (Bio Rad, TLC grade) with ethyl acetate to give Compound 105 as the first fraction (8.7 mg, 28%) to a white powder: m.p. 152°-154° C.; [α]$_D^{25}$ −89.8° (c, 0.15, CHCl₃); IR (film) 3340, 2960, 1734, 1635 cm⁻¹; ¹H NMR (CDCl₃, 500 MHz) 8.11 (1H, d, J=5.5), 7.89 (1H, d, J=9.0), 7.21 (1H, d, J=10.0), 7.06 (2H, d, J=8.5), 6.84 (2H, d, J=8.5), 3.79 (3H, s), 3.12 (3H, s), 2.54 (3H, s); FABMS m/z 1112 (M+H), 295; Anal. Calcd. for: C₅₈H₉₂N₇O₁₄: M$_n$ 1110.6302 (M+H). Found: M$_n$ 1110.6737 (M+H) (HRFABMS).

The second fraction gave Compound 109 (13 mg, 42%); as colorless needles: m.p. 162°-164° C.: [α]$_D^{25}$ −69° (c, 0.89, CHCl₃); IR (film) 3339, 2961, 2874, 1732, 1629 cm⁻¹; ¹H NMR (CDCl₃, 500 MHz) 9.15 (1H, d, J=6.0), 7.92*, 7.87* (1H, d, J=9.0), 7.26*, 7.11* (1H, d, J=10.0), 7.06 (1H, d, J=9.0), 6.84 (2H, d, J=8.5), 3.78 (3H, s), 2.86 (3H, s), 2.54, 2.53 (3H, s), (*Peaks observed as sets); FABMS m/z 1110 (M+H), 295; Anal. Calcd. for: C₅₈H₉₂N₇O₁₄: M$_n$ 1110.6302 (M+H). Found: M$_n$ 1110.6726 (M+H) (HRFABMS).

[L-Ala⁸]didemnin B (Compound 109).

a. O'Benzyl-L-Lactyl-L-Alanine Methyl Ester (Compound 120)

A mixture of O-benzyl-L-lactic acid (57.7 mg, 0.35 mmol), L-alanine methyl ester hydrochloride (50.0 mg, 0.36 mmol) in dichloromethane-dimethylformamide (6:4, 2 ml) was stirred at −10° C. A solution of dicyclohexyl carbodiimide (100 mg, 0.49 mmol) and dimethylamino pyridine (2 mg) in dichlormethane-dimethylformamide (6:4, 2 ml) was added to the mixture, which was allowed to stand at elevated temperatures from −10° C. to 4° C. over 2 hr. then at 4° C. for 30 hr. The reaction mixture was concentrated in vacuo, and the resulting product was suspended in cold ethyl acetate, filtered, and separated on a silica gel column with ethyl acetate to give light yellow oily Compound 120 (81.7 mg, 94%); [α]$_D^{20}$ −20° (c, 1.2, CHCl₃); IR (film) 3400, 3330, 2960, 2870, 1736, 1640, 1535, 1450, 1200, 1170 cm⁻¹; ¹H NMR (CDCl₃, 300 MHz) 7.37-7.32 (5H, m), 7.16 (1H, d, J=7.0), 4.62 (1H, d, J=11.1), 4.54 (1H, d, J=11.1), 4.61 (1H, m), 3.06 (1H, q, J=6.9), 3.75 (3H, s), 1.40 (6H, d, J=6.9); ¹³C NMR (CDCl₃, 75 MHz) 173.27, 173.01, 137.19, 128.59, 128.13, 128.10, 76.03, 72.18, 52.48, 47.35, 18.40. Anal. Calcd. for C₁₄H₁₉NO₄: 266.1392 (M+H). Found 266.1398 (M+H) (HRFABMS).

b. O-Benzyl-L-Lactyl-L-Alanine (Compound 121)

To a sample of Compound 120 (62 mg, 0.25 mmol) in dioxane was added aqueous potassium hydroxide (1N, 300 μl). The mixture was stirred for 12 hr. at room temperature. Hydrochloric acid (1N, 300 μl) was added to the mixture, and the solvent was removed in vacuo. The residual solid was suspended in dichloromethane, filtered, and concentrated in vacuo to give Compound 121 as a light yellow oil (56.9 mg. 98%): [α]$_D^{26}$ −18.8°

(c, 2.11, CHCl₃); IR (Film) 3400, 3330, 2960, 2600, 1736, 1640, 1535, 1450, 1200, 1170 cm⁻⁰¹; ¹H NMR (CDCl₃, 300 MHz) 11.1 (1H, br s), 7.35 (5H, m), 4.62 (1H, d, J=11.1), 4.57 (1H, m), 4.50 (1H, d, J=11.1), 4.00 (1H, q, J=6.6), 1.42 (6H, t, J=6.6); ¹³C NMR (75 MHz, CDCl₃) 176.10, 174.06, 137.07, 128.59, 128.09, 128.12, 75.83, 72.24, 47.87, 18.76, 18.13. Anal. Calcd. for C₁₃H₁₇NO₄: 252.1236 (M+H). Found: 252.1238 (M+H) (HRFABMS).

c. O-Benzyl-[L-Ala⁸]didemnin B (Compound 122)

To a solution of dicyclohexyl carbodiimide (21.5 mg, 0.10 mmol) in dichloromethane (0.5 ml) was added a solution of Compound 121 (22.6 mg, 0.095 mmol) and N-hydroxysuccinimide (31.1 mg, 1.2 mmol) in dichloromethane (1 ml) at −10° C. The mixture, which became a heterogeneous emulsion, was stirred for 1 hr. at −10° C. Compound 1 (81.4 mg, 0.086 mmol) and N-methylmorpholine (9.0 mg, 0.088 mmol) were added to the suspension and the reaction mixture was allowed to stand at −10° C. for 3 hr. then at 4° C. for 24 h. A catalytic amount of dimethylamino pyridine (1 mg) was added to the mixture, and the reaction was continued further for 16 hr. at 4° C. The reaction mixture was concentrated and the residue was suspended in ethyl acetate, filtered, and concentrated in vacuo to give an oil which was chromatographed on a silica gel column with chloroform-methanol (15:1) to give Compound 122 (62 mg), 62%), a white powder: m.p. 106°-108° C.; ¹H NMR (300 MHz, CDCl₃ 7.87 (1H, d, J=9.0), 7.50 (1H, d, J=6.6), 7.35-7.24 (5H, m), 7.18 (2H, m), 7.04 (2H, d, J=8.1), 6.81 (2H, d, J=8.1), 3.75 (3H, s), 3.05 (3H, s), 2.53 (3H, s); FABMS m/z 1176 (M+H), 361. Anal. Calcd. for C₆₂H₉₄N₇O₁₅: $M_n$ 1176.6808 (M+H). Found: $M_n$ 1176.6814 (M+H) (HRFABMS).

d. [L-Ala⁸]didemnin B (Compound 109)

A mixture of Compound 122 (53.2 mg, 0.045 mmol) and palladium on activated carbon (10%, 50 mg) in methanol (2 ml, containing 100 μl of acetic acid) was vigorously stirred in a hydrogen atmosphere for 3 hr. at room temperature. Sodium bicarbonate (10 mg) was added to the mixture. The product was filtered through a C-18 Sep-pak column with methanol, and concentrated to give Compound 109 (47.6 mg, 97%). A portion of Compound 109 was purified by HPLC with methanol-water (7:1); to a white powder: m.p. 144°-146° C.; [α]_D²⁶ −120° (c, 1.31, CHCl₃); IR (film) 3330, 2960, 2874, 1734, 1637, 1514, 1452, 1248 cm⁻¹; ¹H NMR (CDCl₃, 500 MHz) 7.91 (1hr., d, J=9.0), 7.70 (1H, d, J=10.0), 7.30 (1H, d, J=9.5), 7.27 (1H, d, J=6.5), 7.07 (2H, d, J=8.4), 6.84 (2H, d, J=8 4), 5.14 (1H, d, J=3.5, Hip H-4), 5.07 (1H, m, Thr H-), 4.98 (1H, dq, J=8.5, 6.5, Ala H-), 4.83 (1H, br t, J=11.0, Leu H-), 4.76 (1H, dd, 3.0, 8.5, MeLeu H-), 4.71 (1H, br s), 4.56 (1H, dd, J=5.5, 7.5), 4.23 (1H, q, J=6.5, Hip H-2), 4.00 (1H, t, J=10.0), 3.85 (1H, m), 3.79 (3H, s, Me₂Tyr-OCH₃), 3.03 (3H, s, MeLeu NCH₃), 2.53 (3H, s, Me₂Tyr NCH₃), 1.40 (3H, d, J=6.5), 136 (1H, d, J=6.5, Ala-CH₃), 1.35 (3H, d, J=7.0), 1.26 93H, d, J=6.5, Thr-CH₃); ¹³C NMR (CDCl₃, 300 MHz) 204.6, 175.5, 174.6, 174.2, 172.0, 171.2, 171.1, 170.3, 170.2, 169.6, 168.3, 158.6, 130.3, 129.7, 114.1 81.8, 70.5, 68.6, 67.5, 66.1 57.3, 56.3, 55.7, 55.3, 53.9, 49.6, 47.1, 44.6, 41.5, 38.6, 38.1, 35.7, 34.2, 33.8, 33.7, 31.2, 30.2, 27.9, 26.6, 25.3, 25.1, 24.8, 23.7, 22.9, 22.2, 20.9, 20.7, 20.2, 18.5, 17.5, 16.9, 15.5, 14.7, 11.4; FABMS m/z 1087 (M+H), 271; Anal. Calcd. for C₅₅H₈₈N₇O₁₅: $M_n$ 1086.6338 (M+H). Found: $M_n$ 1086.6359 (M+H) (HRFABMS).

[D-Pro⁸]didemnin B (Compound 108).

a. O-Benzyl-L-lactyl-D-proline Methyl Ester (Compound 123)

To a solution of O-benzyl-L-lactic acid (194.4 mg, 1.08 mmol) in dichloromethane (1 ml) was added dicyclohexyl carbodiimide (111.2 mg, 0.54 mmol) at 0° C., and the mixture was stirred for 30 min. D-Proline methyl ester hydrochloride (53.1 mg, 0.32 mmol) and N-methylmorpholine (33.0 mg, 0.33 mmol) in dimethylformamide (1 ml) was added to the suspension and the mixture was allowed to react at 4° C. for 9 hr. The product was filtered, concentrated in vacuo, and then suspended in cold ethyl acetate, filtered and concentrated in vacuo to give an oil which was separated on a silica gel column with ethyl acetate to give Compound 123 (47.6 mg, 44%) as a colorless oil: [α]_D²⁶ = +1.42° (c, 1.83, CHCl₃); IR (film) 2960, 2930, 2870, 1736, 1639, 1450, 1200, 1170, 798 cm⁻¹; ¹³C NMR (300 MHz) 172.63, 171.27, 137.20, 128.37, 128.34, 128.11, 127.75, 73.89, 70.51, 59.20, 52.17, 46.54, 28.55, 25.03, 17.23. Anal. Calcd. for C₁₆H₂₂NO₄: 292.1549 (M+H). Found: 292.1550 (M +H) (HRFABMS).

b. O-Benzyl-L-lactyl-D-proline (Compound 110)

Compound 123 (124.7 mg) in dioxane (1 ml) was treated with aqueous potassium hydroxide (1N, 0.5 ml) at room temperature for 20 hr. The mixture was concentrated to give an aqueous emulsion, which was acidified to pH 2 (HCl), extracted with dichloromethane, dried over sodium sulfate, and evaporated to give an oil (117.9 mg, 100%): IR (film) 3400-2500 br, 1736, 1640 cm⁻¹ Anal Calcd. for C₁₅H₂₀NO₄ (M+H): 278.1392. Found: 278.1394 (M +H) (HRFABMS).

c. O-Benzyl-[D-pro8]didemnin B (Compound 112)

A mixture of Compound 110 (52.4 mg, 0.19 mmol) and dicyclohexyl carbodiimide (19.6 mg, 0.095 mmol) in dichloromethane (1 ml) was stirred at 0° C. for 2 hr. To this suspension was added a solution of Compound 1 (59.7 mg, 0.063 mmol) in dichloromethane (1 ml). The reaction mixture was allowed to stand at 0° C. for 12 hr., and concentrated in vacuo. The residue was suspended in ethyl acetate, filtered, and the product was separated on a silica gel column with ethyl acetate to give Compound 112 (61.9 mg, 83% based on unreacted Compound 1), as a white solid: m.p. 102°-106 ° C.; [α]_D²⁶ −60° (c, 0.38, CHCl₃); ¹H NMR (CDCl₃, 300 MHz) 7.94* (1H, d×2, 6.9, 6.3), 7.22–7.42 (5H, m), 7.13 (1H, d, J=9.9), 7.07 (2H, d, J=8 7), 6.95 (1H, d, J=9.0), 3.79 (3H, s), 2.95 and 2.88* (3H, s), 2.56 and 2.55* (3H, s) (*appearing as sets of signals due to conformers); Anal. Calcd. for C₆₄H₉₆N₇O₁₅: 1202.6664 (M+H). Found: 1202.6671 (M+H) (HRFABMS).

d. [D-Pro⁰]didemnin B (Compound 108)

A mixture of Compound 112 (43.1 mg, 0.036 mmol) and palladium on activated carbon (10%, 40 mg) in ethanol (2 ml) and acetic acid (20 μl) was stirred in a hydrogen atmosphere for 2.5 hr. at room temperature. Sodium bicarbonate (10 mg) was added to the mixture, and the product was filtered, and concentrated in vacuo to give a glass which was purified by HPLC, to give pure Compound 108 (39 mg, 97%), as a white powder: m.p. 150°-154° C.; [α]_D²⁵ −65° (c, 1.15, CHCl₃); IR (film) 3420, 3330, 2960, 2890, 1732, 1635, 1539, 1514, 1456, 1248, 1176 cm$^{-1}$; $^1$H NMR (CDCl$_3$, 500 MHz, mixture of conformers) 8.62:8.57 (3:1, 1/3H, d, s, J=6.5), 7.93, 7.92, 7.86, 7.83 (5:1:4:2, 1H, d, s, J=9/5), 7.29:7.14 (1:1, 1H, d, s, J=10.0), 7.07 (2H, d, J=8.5), 6 97:6.85 (1:4, 2/1H, J=9.5), 6.84 (2H, d, J=8.5), 5.19:5.16 (2:3, 1H, d, s, J=3.5, Hip H-4), 3.79 (3H, s, Me$_2$Tyr-OCH$_3$), 2.94:2.93:2.89:2.88 (5:2:4:1, 3H, singlets), 2.56:2.54 (2:3, 3H, singlets); FABMS m/z 1112 (M+H), 297; Anal. Calcd. for C$_{57}$H$_{90}$N$_7$O$_{15}$: M$_n$ 1112.6491 (M+H). Found: M$_n$ 1112.6493 (M+H) (HRFABMS).

Hydroxysuccinimide Adduct of Didemnin A, [N-(CH$_3$ONsu)didemnin A (Compound 111)

To a stirred mixture of O-benzyl-L-lactyl-D-proline (Compound 110, 28.8 mg, 0.104 mmol) and dried N-hydroxysuccinimide (16.6 mg, 0.146 mmol) in dichloromethane (0.5 ml) was added a solution of dicyclohexyl carbodiimide (30.1 mg, 0.146 mmol) in dichloromethane at −10° C., and the mixture was allowed to stand for 1.5 hr. To the mixture was added a solution of Compound 1 (89.1 mg, 0.095 mmol) and N-methylmorpholine (105 mg, 0 104 mmol) in dichloromethane (1 ml). The reaction mixture was allowed to react at 4° C. for 24 hr. Dimethylaminopyridine (1 mg) was added to the mixture, and the reaction was continued for 24 hr. Solvent was removed in vacuo, and the residual solid was separated on a silica gel column to give Compound 111 as a white powder (25.3 mg, 22%, HPLC on C-18, 7:1 methanol-water, retention time 14.6 min.), m.p. 120°–124° C.; [α]$_D^{26}$−93° (c, 0.90, CHCl$_3$); IR (film) 3330, 2960, 1734, 1639, 1539, 1514, 1170 cm$^{-1}$; $^1$H NMR (500 MHz, CDCl$_3$) 7.98 (1H, d, J=9.0), 7.2–7.4 (3H, m), 7.06 (2H, d, J=8/7), 6.83 (2H, d, J=8.7), 3.77 (3H, s), 2.70 (3H, s), 2.54 (3H, s); $^{13}$C NMR (CDCl$_3$, 75 MHz) 204.8 (s), 173.7 (s), 173.4 (s), 172.2 (s), 171.2 (s), 170.4 (s), 169.7 (s), 168.3 (s), 159.6 (s), 158.6 (s), 130.3 (d), 129.8(s), 114.1 (d), 81.7 (d), 70.6 (d), 67.9 (d), 57.3 (d), 55.6 (d), 55.7 (d), 55.3 (q), 54.4 (d), 51.7 (q), 49.8 (d), 49.6 (d), 47.4 (t) 41.4 (t) 38.4 (q), 38.6 (t), 36.6 (t) 36.2 (t), 34.2 (d), 34.1 (t), 34.0 (t), 31.4 (d), 29.4 (q), 27.9 (t), 26.7 (t), 25.1 (t) 24.8 (d), 24.7 (d), 23.7 (q), 23.0 (q), 22.2 (q), 20.9 (q), 18.5 (q), 16.9 (q), 15.3 (q), 15.2 (q), 15.0 (q), 11.5 (g); multiplicities determined by DEPT experiments); FABMS m/z 1073 (M+H), 943, 816, 257, 229, 164; Anal. Calcd. for C$_{54}$H$_{86}$N$_7$O$_{15}$: 1072.6182 (M+H) Found: 1072.6204 (M+H) (HRFABMS).

O-Pyroglutamyldidemnin B (Compound 113)

To a mixture of Compound 17 (230 mg, 0.21 mmol) and L-pyroglutamic acid (134 mg, 1.04 mmol) in dimethylformamide (5 ml) were added dicyclohexyl carbodiimide (206 mg, 1.00 mmol) and dimethylamino pyridine (6 mg) at room temperature. The mixture was stirred for 20 hr. at room temperature. Water (50 ml) and dichloromethane (50 ml×3) were added to the reaction mixture, and the organic layer was concentrated in vacuo. The resulting solid was separated on a silica gel column with ethyl acetate-2-propanol (10:1) to give recovered Compound 17 (77 mg, 33%) and Compound 113 (135 mg, 53% conversion), as a white powder (HPLC on C-18, 7:1 methanol-water, retention time 7.0 min.); m.p. 158°–162° C.; [α]$_D^{20}$−79° (c, 1.4, CHCl$_3$); IR (film) 3390, 2974, 1730, 1651, 1452, 1252 cm$^{-1}$: 7.77 (1H, d, J=9.0), 7.57 (1H, d, J=5.1), 7.23 (1H, d, J=9.3), 7.06 (2H, d, J=8.7), 6.80 (2H, d, J=8.7), 3.76 (3H, s), 3.10 (3H, s), 2.54 (3H, s); FABMS m/z 1224 (M +H), 1113, 447, 275, 195; Anal. Calcd. for C$_{62}$H$_{95}$N$_8$O$_{17}$ (M+H): M$_n$ 1223.6384. Found: M$_n$ 1223.6365 (M+H) (HRFABMS).

O-Acetyldidemnin A (Compound 114)

To a solution of Compound 1 (55.2 mg, 0.059 mol) in benzene (0.8 ml) was added benzyloxycarbonyl chloride (50 μl, 6 eq.) and triethylamine (10 μl). The mixture was allowed to react at room temperature for 24 hr., and concentrated by N$_2$, and the resulting solid was separated on a short (4 g) silica gel column (Bio Rad, TLC grade) with ethyl acetate to give N-Z-didemnin A upon evaporation of the solvent. The product was further treated with pyridine (0.5 ml) and acetic anhydride (0 5 ml) for 12 hr. at room temperature to give N-Z-(O-acetyl) didemnin A (63 mg, 92%): 1H NMR (CDCl$_3$, 300 MHz) 7.36 (5H, m), 7.08 (2H, d, J=8.4), 6.85 (2H, d, J=8.4), 3.80 (3H, s), 2.86 (2H, br s), 2.55 (3H, s), 2.17 (3H, s), 1.97 (3H, s). Anal. Calcd. for C$_{59}$H$_{87}$N$_6$O$_{15}$ (M+H): M$_n$ 1119.6229. Found: M$_n$ 1119.6217 (M+H) (HRFABMS).

A mixture of N-Z-(O-acetyl) didemnin A (40 mg 0.035 mol) and platinum on activated carbon (10%, 40 mg) in 2-propanol (1 ml) and acetic acid (10 μl) was stirred in a hydrogen atmosphere for 2.5 hr. at room temperature. The product was filtered through a short (4 g) silica gel column with ethyl acetate-2-propanol (4:1), and concentrated, and the residue was purified by HPLC on silica gel with ethyl acetate to give Compound 114 as the first peak (6 mg, 17%), a white powder: m.p. 118°–120° C.; [α]$_D^{24}$=−136.1° c, 0.38, CHCl$_3$); IR (film) 3319, 2959, 1734, 1653, 1635 cm$^{-1}$; $^1$H NMR (300 MHz) 8.26 (1H, d, J=9.0), 7.72 (1H, d, J=9.3), 7.37 (1H, d, J=9.2), 7.08 (2H, d, J=8.4), 6.85 (2H, d, J=8.4), 3.80 (3H, s), 2.55 (3H, s), 2.38 (3H, s), 1.97 (3H, s); FABMS m/z 986 (M+H); Anal. Calcd. for C$_{51}$H$_{81}$N$_6$O$_{13}$: M$_n$ 985.5861 (M+H). Found: M$_n$ 985.5871 (M+H) (HRFABMS).

The second peak gave Compound 97 (6 mg, 17%), as a white powder: m.p. 120°–124° C.; [α]$_D^{24}$−72° (c, 0.34, CHCl$_3$); IR (film) 3327, 2961, 1749, 1662, 1653, 1635 cm$^{-1}$; $^1$H NMR (300 MHz) 8.05 (1H, d, J=9.0), 7.60 (1H, d, J=8.7), 7.20 (1H, d, J=9.9), 7.08 (2H, d, J=8.4), 6.85 (2H, d, J=8.4), 3.80 (3H, s), 2.57 (3H, s), 2.37 (3H, s), 1.99 (3H, s); FABMS m/z 988; Anal. Calcd. for C$_{51}$H$_{83}$N$_6$O$_{13}$ (M+H): M$_n$ 987.6108. Found M$_n$ 987.6023, (M+H) (HRFABMS).

[HexahydroMe$_2$Tyr$^5$]didemnin A (Compound 115) and [Hexahydro-N-MePhe$^5$]didemnin A (Compound 117)

A mixture of Compound 1 (31.0 mg, 0.33 mmol), platinum on activated carbon (10%, 38.3 mg), and trifluoroacetic acid (20 μl) in methanol (5 ml) stirred in a hydrogen atmosphere for 4 hr. at room temperature. The mixture was filtered through a C-18 column (Seppak) with methanol, and concentrated to give a solid (33.1 mg), which was separated by HPLC (C-18) with methanol-aqueous sodium chloride (0.4M) (7:1) to give Compound 115 (10.7 mg, 34%) from Fraction 1, as a white powder: m.p. 162°–164° C.; [α]$_D^{24}$−97° (c, 0.56, CHCl$_3$); IR (film) 3325, 1740, 1664, 1635, 1550, 1514, 1450, 1245, 1219, 1169 cm$^{-1}$; $^1$H NMR (CDCl$_3$, 500 MHz) 3.30 (3H, s, OCH$_3$), 3.09 (3H, s); FABMS m/z 949; Anal. Calcd. for C$_{49}$H$_{85}$N$_6$O$_{12}$ (M+H): M$_n$ 949.6225. Found: M$_n$ 949.6237, (M+H) (HRFABMS).

Fraction 2 gave Compound 117 (9.3 mg, 31%), as a white powder: m.p. 168°–172° C.; [α]$_D^{24}$−73° (c, 0.43, CHCl$_3$); IR (film) 3330, 2959, 2928, 1734, 1637, 1541, 2269 cm$^{-1}$; UV (2-propanol) $_{max}$ 204 (log 4.46), 230 (4.51) nm; FABMS m/z 919; Anal. Calcd. for C$_{48}$H$_{83}$N$_6$O$_{11}$ (M+H): M$_n$ 919.6120. Found: M$_n$ 919.6139, (M+H) (HRFABMS).

[HexahydroMe$_2$Tyr$^5$]didemnin B (Compound 116) and [Hexahydro-N-MePhe$^5$]didemnin B (Compound 118)

Compound 17 (16.3 mg, 0.015 mmol) was reduced as above to give Compound 116 (3.3 mg, 19.6%), as a white powder: m.p. 144°-147° C.; [α]$_D^{23-29}$ (c, 0.41, CHCl$_3$); IR (film) 3331, 2959, 2928, 2876, 1734, 1638, 1541, 1450 cm$^{-1}$; UV (2-propanol) $_{max}$ 204 (log 4.62) nm; $^1$H NMR (CDCl$_3$, 500 MHz) 7.83 (1H, d, J=9.5), 7.64 (1H, d, J=5.00), 7.22 (1H, d, J=9.5), 3.30 (3H, s), 3.14 (3H, s), 3.12 (3H, s); FABMS m/z 1118 (M +H), 297; Anal. Calcd. for C$_{57}$H$_{96}$N$_7$O$_{15}$ (M+H): M$_n$ 1118.6964. Found: M$_n$ 1118.7001, (M+H) (HRFABMS).

Fraction 2 yielded Compound 118 (5.2 mg, 32%), as a white solid: m.p. 146°-148° C.; [α]$_D^{24-29}$ (c, 0.41, CHCl$_3$); IR (film) 3327, 2959, 2930, 2874, 1736, 1637, 1535, 1450, 1203, 1170 cm$^{-1}$; Uv (2-propanol) $_{max}$ 204 (log 4.40) nm; $^1$H NMR (CDCl$_3$, 500 MHz) 7.82 (1H, d, J=9.5), 7.66 (1H, d, J=5.0), 7.23 (1H, d, J=9.5); FABMS m/z 1088.297; Anal. Calcd. for C$_{56}$H$_{94}$N$_7$O$_{14}$ (M+H): M$_n$ 1088.6859. Found: M$_n$ 1088.6902, (M+H) (HRFABMS).

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. A pharmaceutical composition comprising a didemnin, in combination with a pharmaceutically acceptable carrier, excipient or diluent.

2. The pharmaceutical composition of claim 1, wherein the didemnin is an N-acylated Didemnin A.

3. The pharmaceutical composition of claim 2, wherein the acyl group of the N-acyl Didemnin A comprises a C$_3$ to C$_8$ group.

4. The pharmaceutical composition of claim 1, wherein the didemnin is a synthetic derivative of Didemnin A, modified at a position selected from the group consisting of position 1, 5, 6, and combinations thereof, by the incorporation of a D-amino acid.

5. The pharmaceutical composition of claim 4, wherein the Didemnin A D-amino acid derivative is selected from the group consisting of didemnin A, didemnin A, or didemnin A.

6. The pharmaceutical composition of claim 1, wherein the didemnin is a synthetic derivative of Didemnin A, modified to include a Dehydrodidemnin B (DDB) moiety in the linear peptide chain.

7. The pharmaceutical composition of claim 6, wherein the didemnin is selected from the group consisting of phenylpyruv-Pro didemnin A, Pyruv-Sar didemnin A, alpha-ketobutyryl-Pro didemnin A, Pyruv-Azt didemnin A, or Pyruv-D-Pro didemnin A.

* * * * *

Disclaimer

5,294,603 — Kenneth L. Rinehart, Urbana, Ill. PHARMACEUTICAL COMPOSITIONS CONTAINING DIDEMNINS. Patent dated Mar. 15, 1994. Disclaimer filed Jul. 25, 2005, by the assignee, The Board of Trustees The University of Illinois.

Hereby enters this disclaimer to claim 6, of said patent.

*(Official Gazette, October 11, 2005)*